US011857698B2

(12) United States Patent
Kent et al.

(10) Patent No.: US 11,857,698 B2
(45) Date of Patent: Jan. 2, 2024

(54) BONE GRAFT SYSTEM

(71) Applicant: UCL BUSINESS LTD, London (GB)

(72) Inventors: Niall Kent, London (GB); Marc-Olivier Coppens, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 15/747,080

(22) PCT Filed: Jul. 22, 2016

(86) PCT No.: PCT/GB2016/052221
§ 371 (c)(1),
(2) Date: Jan. 23, 2018

(87) PCT Pub. No.: WO2017/013440
PCT Pub. Date: Jan. 26, 2017

(65) Prior Publication Data
US 2018/0311412 A1 Nov. 1, 2018

(30) Foreign Application Priority Data
Jul. 23, 2015 (GB) .................................... 1513040

(51) Int. Cl.
A61L 27/40 (2006.01)
A61L 27/56 (2006.01)
A61L 27/42 (2006.01)
A61L 27/52 (2006.01)

(52) U.S. Cl.
CPC ............. A61L 27/40 (2013.01); A61L 27/425 (2013.01); A61L 27/427 (2013.01); A61L 27/52 (2013.01); A61L 27/56 (2013.01); A61L 2430/02 (2013.01)

(58) Field of Classification Search
CPC ...... A61L 27/40; A61L 27/56; A61L 2430/02; A61L 27/52; A61L 27/427; A61L 27/425
See application file for complete search history.

(56) References Cited

U.S. PATENT DOCUMENTS

| 5,735,942 | A | * | 4/1998 | Litkowski | ............. | C03C 4/0021 106/35 |
| 6,482,444 | B1 | * | 11/2002 | Bellantone | ............ | A61L 17/005 424/618 |
| 2005/0226904 | A1 | * | 10/2005 | Choi | ........................ | A61L 27/18 424/443 |
| 2007/0059379 | A1 | | 3/2007 | Gerber | | |
| 2008/0152723 | A9 | | 6/2008 | Gerber | | |
| 2011/0000370 | A1 | | 1/2011 | Norberg et al. | | |

FOREIGN PATENT DOCUMENTS

| CN | 1826147 A | 8/2006 | | |
| DE | 10323079 A1 | 12/2004 | | |
| DE | 10338634 A1 | 3/2005 | | |
| EP | 2894425 A1 | 7/2015 | | |
| WO | WO-0205750 A2 | * | 1/2002 | ........... A61B 17/866 |
| WO | 2007025698 A2 | 3/2007 | | |

OTHER PUBLICATIONS

Thimm et al. "Biocompatibility studies of endothelial cells on a novel calcium phosphate/SiO2-xerogel composite for bone tissue engineering", Biomedical Materials, 3 (1) (2008), 15007.
Hench LL. The story of Bioglass (R). J Mater Sci-Mater M 2006;17:967-78.
Jones JR. Review of bioactive glass: From Hench to hybrids. Acta Biomater 2013;9:4457-86.
Fujikura K, Karpukhina N, Kasuga T, Brauer DS, Hill RG, Law RV. Influence of strontium substitution on structure and crystallisation of Bioglass (R) 45S5. J Mater Chem 2012;22:7395-402.
Fredholm YC, Karpukhina N, Brauer DS, Jones JR, Law RV, Hill RG. Influence of strontium for calcium substitution in bioactive glasses on degradation, ion release and apatite formation. J R Soc Interface 2012;9:880-9.
Brauer DS, Karpukhina N, O'Donnell MD, Law RV, Hill RG. Fluoride-containing bioactive glasses: Effect of glass design and structure on degradation, pH and apatite formation in simulated body fluid. Acta Biomater 2010;6:3275-82.
Fredholm YC, Karpukhina N, Law RV, Hill RG. Strontium containing bioactive glasses: Glass structure and physical properties. J Non-Cryst Solids 2010;356:2546-51.
Amato MM, Blaydon SM, Scribbick FW, Belden CJ, Shore JW, Neuhaus RW, et al. Use of bioglass for orbital volume augmentation in enophthalmos: A rabbit model (*Oryctolagus cuniculus*). Ophthal Plast Recons 2003;19:455-65.
Sakka S, Kamiya K. The Sol-Gel Transition in the Hydrolysis of Metal Alkoxides in Relation to the Formation of Glass-Fibers and Films. J Non-Cryst Solids 1982;48:31-46.
Gil-Albarova J, Garrido-Lahiguera R, Salinas AJ, Roman J, Bueno-Lozano A, Gil-Albarova R, et al. The in vivo performance of a sol-gel glass and a glass-ceramic in the treatment of limited bone defects. Biomaterials 2004;25:4639-45.
Toledo-Fernandez JA, Mendoza-Serna R, Morales V, de la Rosa-Fox N, Pinero M, Santos A, et al. Bioactivity of wollastonite/ aerogels composites obtained from a TEOS-MTES matrix. J Mater Sci-Mater M 2008;19:2207-13.
Straumann 2014 Annual Report referencing a Straumann proprietary study based on 5000 respondents conducted by AFG Research in 2012.

(Continued)

Primary Examiner — Aradhana Sasan
(74) Attorney, Agent, or Firm — Stites & Harbison PLLC; Richard S. Myers, Jr.

(57) ABSTRACT

The present invention relates generally to the field of bone graft substitutes and methods for making the same, particularly the invention relates to bone graft substitutes for use in dental or orthopaedic implants. The bone graft substitutes described herein comprise a silicate based material. The silicate based material is a silicate network with a porous structure. The silicate network has one or more metal cations incorporated therein. Preferably a phosphate is also incorporated into the silicate network. The bone graft substitute may have a low density, preferably a density of less than 1.1 g/cm³. The bone graft substitute may be an aerogel or a cryogel.

47 Claims, 8 Drawing Sheets

(56) References Cited

OTHER PUBLICATIONS

Müller, F., Naharro, M. and Carlsson, G. E. (2007), What are the prevalence and incidence of tooth loss in the adult and elderly population in Europe?. Clinical Oral Implants Research, 18: 2-14.
Rajesh, et al., Assessment of salivary calcium, phosphate, magnesium, pH, and flow rate in healthy subjects, periodontitis, and dental caries; Contemp Clin Dent 2015, 6: pp. 461-465.

* cited by examiner

BONE GRAFT SYSTEM

CROSS REFERENCE TO RELATED APPLICATIONS

This application is a § 371 National State Application of PCT/GB2016/052221, filed Jul. 22, 2016 which claims priority to GB 1513040.4, filed Jul. 23, 2015.

TECHNICAL FIELD

The present invention relates to bone graft substitutes, particularly to bone graft substitutes for use in dental or orthopaedic implants.

BACKGROUND OF THE INVENTION

An orthopedic implant is a medical device manufactured to replace a missing joint or bone or to support a damaged bone Dental implants are an increasingly popular choice for replacement of missing teeth. Their popularity may be due to their ability to restore function and aesthetics. This in turn may contribute to the social and emotional well-being of a subject.

After tooth extraction, in an ungrafted site, the alveolus may shrink causing problems with implant placement due to insufficient bone on which to graft the implant.

In many cases the bone defect is too extensive to achieve primary stability of the implant. To overcome this issue, extraction sockets are filled with bone graft substitute immediately after tooth extraction to minimise bone shrinkage during healing or repair the bone defect at the time of implant placement.

Depending on the clinical procedure being performed, the in-vivo requirements of a graft material may fall into one of two categories: (1) rapid bone remodelling (resorption and replacement of the material by new bone) within three to six months, or (2) virtually non-resorbable, with little to no remodelling.

In both cases (rapid bone remodelling and no remodelling) high levels of osseointegration are also required.

The ability to control the remodelling rate of a bone graft material allows a graft material to be used effectively in a wide range of clinical situations.

Currently used synthetic bone graft substitutes typically consist of calcium phosphate salts or minerals, typically hydroxyapatite ($Ca_{10}(PO_4)_6(OH)_2$), tricalcium phosphate ($Ca_3(PO_4)_2$) or mixtures thereof.

For both dentistry and orthopaedics these are generally formed into sub-millimetre sized porous granules that are implanted by mixing with the patients' blood and then packed into the implant site.

The problems with calcium phosphate bone graft substitutes are primarily their long resorption times and low osseointegration. These low osseointegration rates create a higher probability of implant failure.

Bioactive glasses have been investigated for their ability to provide alternative bone graft substitutes.

Bioactive glasses are silicate based amorphous solid materials typically containing a source of calcium and phosphate that once mixed with body fluids precipitate hydroxyapatite on their surface.

Advantages of bioactive glasses are that they have high rates of osseointegration (>90%) and are both resorbed by osteoclast action and dissolved at physiological pH.

There are two main types of bioactive glass, melt-quench and sol-gel derived.

Melt-quench derived bioactive glasses are typically produced in furnaces at 1300-1500° C. and quenched in water. Melt-quench derived glasses typically have densities of 1.5-2.5 $gcm^{-3}$, significantly higher than sol-gel derived glasses due to their absences of silanol groups and any material porosity. CE marked bone graft substitute products which are melt-quench bioactive glasses include, NovaBone and StronBone.

Unlike melt-quench bioactive glasses, sol-gel bioactive glasses do not require high temperatures during synthesis and can be produced in the absence of sodium. They have slightly lower density (0.8-1.1 g $cm^{-3}$) than melt-quench derived glasses and are mesoporous. Sol-gel glasses have in the past been cast into discs, however, these have been shown to be prone to cracking and can only be made to limited dimensions due to difficulty in drying. A number of studies have assessed the performance of sol-gel derived bioactive glasses in-vivo. Typically these studies have had very positive results with respect to osseointegration (>90%) and osteoinduction.

Whilst having the potential to be excellent bone grafting materials, bioactive glasses suffer from two major disadvantages which have inhibited their clinical uptake: Relatively slow resorption times and high pH build-up within implant site. In particular, as discussed above, there is a clinical need for both fast and slow remodelling rates, equating to either around 3-6 months or 6-8+ years. Recent studies have shown that the remodelling occurs within 1-3 years for bioactive glasses. This rate does not sit in the desirable range for either clinical need. Furthermore with bioactive glasses a build-up of pH within the implant site is also observed. This is thought to be due to the ion exchange process that occurs when bioactive glasses are immersed in aqueous solution. The build-up in pH has been shown to result in 'hollow' implant sites where the glass has been resorbed but no bone has grown in. This can cause insufficient bone restoration, thereby limiting the ability to fit an implant.

Two widely used dental bone grafting products are BoneCeramic (synthetic, calcium phosphate based) and Bio-Oss (xenograft, bovine derived).

Both of these products have relatively slow remodelling rates, with substantial amounts of material having been shown to remain after nine months. Implants fitted in such scenarios are therefore seated partly in new bone and partly in granular grafting material, reducing their stability. In the case of dental grafts it is preferred that the remodelling rate is 3-6 months (remodelling rate 1 discussed above).

Further studies have shown these products to have relatively low osseointegration rates, 48.2% for Bio-Oss and 34.0% for BoneCeramic, which is further likely to limit implant stability.

Currently, around 1 in 10 implants fail, leading to significant pain and remedial surgery. This remedial surgery can cost around £3,000-£5,000, either to the patient, a health service provider (such as the NHS) or an insurance provider. Thus it can be seen that improved graft stability and\or reduced implant failure would be beneficial in terms of reduced cost and the reduction of patient chairside time and distress.

More generally, it is desirable to provide a bone graft substitute that exhibits one or more improved properties of high osteoconduction (provision of a conductive lattice), high osseointegration (integration of the bone and graft material), resorption (of the graft material), high osteoinduction and successful bone regeneration. Improvements of these properties would result in improved graft and implant stability.

Further, it is desirable to provide the ability to tailor the properties of a bone graft substitute to suit a particular clinical need, for example, by tailoring the resorption rate to suit a particular graft site. The tailoring of a graft for a particular use should have the potential to increase stability and reduce implant failure.

US 2008/0152723 and US 2007/0059379 discuss silicate based xerogels with crystalline calcium phosphate embedded therein. These materials are discussed for use in bone graft applications. US 2008/0152723 and US 2007/0059379 do not disclose a silicate based material with the properties of the present invention.

Fernandez et al. discusses a mesoporous wollastonite coated silicate aerogel. The silicate aerogel is produced via the sol-gel method followed by supercritical drying (Toledo-Fernandez J A, Mendoza-Sema R, Morales V, de la Rosa-Fox N, Pinero M, Santos A, et al. Bioactivity of wollastonite/aerogels composites obtained from a TEOS-MTES matrix. J Mater Sci-Mater M 2008; 19:2207-13). The material is a composite containing a crystalline form of calcium silicate (wollastonite, $CaSiO_3$) and polydimethyl siloxane (PDMS) polymer. The composite material requires acidic conditions, around pH 1, during synthesis.

The composite material of Fernandez et al. is shown to induce the formation of an apatite like structure on its surface after being immersed in simulated body fluid for 25 days. The composite materials require surface activation and this is carried out by treating the composite material under alkaline conditions.

Nevertheless it can be seen that the provision of novel bone graft materials having improved properties, such as any of those properties described above, would provide a contribution to the art.

DISCLOSURE OF THE INVENTION

The present invention provides a bone graft substitute that addresses one or more of the problems outlined in the prior art.

In one aspect the present invention provides a bone graft substitute comprising a silicate based material which is a silicate network having one or more metal cations incorporated into the silicate network. The bone graft substitute has a porous structure. In some embodiments the bone graft substitute has a density of less than 1.1 $g/cm^3$. In some embodiments the bone graft substitute of the present invention is an aerogel or a cryogel.

Preferably a phosphate is also incorporated into the silicate network.

A further aspect of the present invention is a process of making a bone graft substitute comprising a gel formation stage; a gel drying stage and a calcination stage.

A further aspect of the present invention provides a bone graft substitute obtainable by a process comprising a gel formation stage; a gel drying stage and a calcination stage.

A further aspect of the invention provides use of the bone graft substitutes of the invention in dental, medical or oral healthcare applications.

A further aspect of the invention provides a composition comprising the bone graft substitutes of the present invention and at least one other biomaterial.

A further aspect of the invention provides use of the bone graft substitutes of the invention in combination with other biomaterials.

A further aspect of the invention provides a method of treatment or surgery comprising implanting a bone graft substitute of the present invention into a subject.

A further aspect of the invention provides a method of promoting bone growth by treating a bone graft substitute of the present invention under physiological conditions.

In a further aspect of the present invention the bone graft substitutes of the present invention are used as vehicles for drug delivery.

A further aspect the present invention provides a method of promoting bone formation by implanting a bone graft substitute of the present invention.

The options, features, preferences and so on mentioned herein apply both independently and in any combination, except where such a combination is expressly prohibited or clearly impermissible.

Bone Graft Substitutes

One aspect of the present invention provides a bone graft substitute comprising a silicate based material having a metal cation incorporated into the silicate based material. The silicate based material is a silicate network. The bone graft substitute has a porous structure. Preferably, the bone graft substitute has a density of less than 1.1 $g/cm^3$.

Preferably, a phosphate is also incorporated into the silicate based material.

In some embodiments the bone graft substitute of the present invention comprises a porous solid derived from a gel wherein the dispersed phase is a gas, which is typically air. For example, the bone graft substitute may be an aerogel or a cryogel.

The term aerogel as used herein encompasses porous solids wherein the dispersed phase is a gas that are most commonly made by supercritical drying of a gel having a liquid dispersed phase.

The term cryogel as used herein encompasses porous solids wherein the dispersed phase is a gas that are made by freeze drying of a gel having a liquid dispersed phase.

Both of these materials may, for brevity, be referred to as "gels" or "solid gels" herein.

These porous solid gels (wherein the dispersed phase is a gas such as air) exhibit ultra-low density. When the bone graft substitute comprises a porous solid gel, the silicate based material is the porous solid gel.

The bone graft substitutes of the present invention are highly porous, ultra-low density and silicon-based materials. These materials are suitable for biomedical applications.

Without wishing to be bound by theory it is suggested that the bone graft substitutes of the present invention work by incorporating various monovalent or divalent metal cations, (often calcium) and optionally phosphate into the silicate network.

It is proposed that the metal cations are ionically bound to the silicate network via an oxygen anion. The oxygen anion may also be covalently bonded to a tetrahedral silicon atom (scheme 1A). Once immersed into an aqueous solution the metal cations are released (scheme 1B) and may precipitate hydroxyapatite ($Ca_{10}(PO_4)_6(OH)_2$ or carbonate substituted apatite, the mineral phase of bones and teeth. FIG. 5 shows scheme 1.

Without wishing to be bound by theory it is proposed that the phosphate, if present, may be ionically bound to the silicate network via one or more of the metal cations (structure 1) which are present in the silicate network. The phosphate may exist as a $PO_4^{3-}$ anion. FIG. 6 shows structure 1.

It has also been proposed that the phosphate may be covalently bound to the silicate network via a Si—O—P covalent bond.

The bone graft substitutes of the present invention provide improved resorption properties due to the presence of silicate material and the low density (which means less graft material is present to be resorbed).

The remodelling rate of the bone graft substitutes of the present invention can be tailored by controlling, for example, the density. This allows the bone graft substitutes of the present invention to be used in a wide range of clinical situations and further, to be particularly effective in each specific clinical situation.

Due to the low density of the bone graft materials of the present invention a build-up of pH within the implant site may be avoided. Lower density means less bone graft material is present to undergo the ion exchange processes which have been proposed to cause the rise in pH observed with bioactive glasses.

The bone graft substitutes of the present invention may provide high rates of osseointegration that are associated with silicate based graft materials.

The bone graft substitutes of the present invention may exhibit rapid formation of apatite, for example, apatite may be formed in less than 24 hours.

Composition

The bone graft substitutes of the present invention comprise silicate based materials having a metal cation incorporated into the silicate based material. Preferably a phosphate is also incorporated into the silicate based material.

The silicate based materials having a metal cation incorporated may be substantially amorphous. Preferably, the silicate based materials having a metal cation incorporated may be entirely amorphous.

The term amorphous is used herein to describe a material which lacks the long-range order characteristic of a crystal. Amorphous materials may have some short-range order at the atomic length scale.

The term silicate based material as used herein refers to a material containing silicate.

In some embodiments the silicate based material contains silicon oxides or silicon fluorides. Preferably the silicate based material contains silicon oxides.

The silicate based material may contain 20 to 80 mole percent, preferably 30 to 55 mole percent, more preferably 35 to 50 mole percent of silicate (e.g. $SiO_2$).

In some embodiments the silicate based material contains silicon atoms in a tetrahedral or octahedral environment. Preferably the silicate based material contain silicon atoms in a tetrahedral environment.

In some embodiments the silicate based material comprises a chain, sheet or three-dimensional framework of silicates. Preferably the silicate based material is a three-dimensional framework. Preferably the silicate based material comprises $SiO_2$. The Si may be tetrahedral, preferably the Si is quaternary.

The silicate based material forms a silicate network. The silicate network refers to the structure of the silicate which is disrupted by the incorporation of one or more metal ions and optionally phosphate. For example, the silicate network refers to the chain, sheet or three-dimensional framework of the silicate based material. Preferably the silicate network is a three-dimensional framework. Preferably the silicate network comprises $SiO_2$. The Si may be tetrahedral, preferably the Si is quaternary.

For example, if the silicate network is a three-dimensional framework comprising $SiO_2$ where the Si is tetrahedral, the one or more metal ions may be ionically bound to one or more oxygen ions wherein the oxygen ion is also covalently bonded to a tetrahedral silicon atom.

The silicate network comprises silicate, metal ions and optionally phosphate. The silicate network may contain between 0.01 and 70 mole percent of metal cation. For example the silicate network may contain between 1 and 70 moles percent, preferably 10 to 70 mole percent, preferably 30 to 65 mole percent, more preferably 45 to 60 mole percent of metal cation.

The silicate network may contain 1 to 20 mole percent of phosphate, preferably 3 to 10 mole percent of phosphate, more preferably 5 to 7 mole percent of phosphate.

In some embodiments, the silicate network may contain other atoms or groups in addition to the silicate, metal ions and optional phosphate.

The bone graft substitute may have a $SiO_2$ content below 60 mole percent.

The bone graft substitute may have a $SiO_2$ content between 20 and 55 mole percent, preferably between 35 and 50 mole percent.

Silicate-based bioactive materials have been shown to have higher rates of osseointegration than both calcium phosphate based synthetics and xenografts.

The bone graft substitutes of the present invention have a metal cation incorporated into the silicate based material.

The metal cation may be selected from a calcium, strontium, sodium, zinc, magnesium, potassium, titanium, cobalt, aluminium or silver cation. Preferably the metal cation is selected from calcium, strontium or sodium. The bone graft substitute may contain only one metal cation or a mixture of two or more metal cations.

The silicate based material may contain 0.01 and 70 moles percent of metal cation. For example the silicate based material may contain between 1 and 70 moles percent, preferably 10 to 70 mole percent, preferably 30 to 65 mole percent, more preferably 45 to 60 mole percent of metal cation.

In some embodiments the metal cation is ionically bonded to the silicate network via an oxygen anion.

In some embodiments the metal cation may be monovalent or divalent.

The metal cation may be calcium. In some embodiments the calcium cation may be in the form of calcium oxide. The silicate based material may contain 10 to 70 mole percent, preferably 30 to 65 mole percent, more preferably 45 to 60 mole percent of calcium oxide (e.g. CaO).

The metal cation may be strontium. In some embodiments the strontium cation may be strontium oxide. The silicate based material may contain 10 to 70 mole percent, preferably 30 to 65 mole percent, more preferably 45 to 60 mole percent of strontium oxide (e.g. SrO).

In some embodiments the metal cation is derived in whole or in part from any one of hydroxyapatite $(Ca_{10})(PO_4)_6(OH)_2)$, hydroxycarbonatedapatite octacalcium phosphate $(Ca_8H_2(PO_4)_6 \cdot 5H_2O)$, Brushite $(CaHPO_4 \cdot 2H_2O)$, monetite $(CaHPO_4)$, fluorapatite $(Ca_{10})(PO_4)_6F_2)$, chlorapatite $(Ca_{10})(PO_4)_6Cl_2)$, Fluorohydroxyapatite $(Ca_{10}(PO_4)_6(OH)_{2-x}F_x)$, tetracalcium phosphate $(Ca_4(PO_4)_2O)$, tricalcium phosphate $(Ca_3(PO_4)_2)$ or any combination thereof.

In some embodiments a phosphate is incorporated into the silicon based material.

Preferably, the phosphate is an oxide of phosphorus, for example, it may be $PO_4^{3-}$.

When discussing the composition of the bone graft substitutes of the present invention the term $P_2O_5$ may be used to refer to the phosphate. This is a common term in the art used for describing phosphates in compositions (see, for example, the field of bioactive glasses). As those skilled in the art will appreciate, this terminology should not be taken as requiring that the phosphate in the composition is in the form of $P_2O_5$.

In some embodiments the phosphate is incorporated into the silicate network via the metal cations.

In some embodiments the phosphate is covalently bound to the silicate network via a Si—O—P covalent bond.

The silicate based material may contain 1 to 20 mole percent, preferably 3 to 10 mole percent, more preferably 5 to 7 mole percent of phosphate (e.g. $P_2O_5$).

In some embodiments the phosphate is derived in whole or in part from any one of hydroxyapatite $(Ca_{10})(PO_4)_6(OH)_2)$, hydroxycarbonatedapatite octacalcium phosphate $(Ca_8H_2(PO_4)_6 \cdot 5H_2O)$, Brushite $(CaHPO_4 \cdot 2H_2O)$, monetite $(CaHPO_4)$, fluorapatite $(Ca_{10})(PO_4)_6F_2)$, chlorapatite $(Ca_{10})(PO_4)_6Cl_2)$, Fluorohydroxyapatite $(Ca_{10}(PO_4)_6(OH)_{2-x}F_x)$, tetracalcium phosphate $(Ca_4(PO_4)_2O)$, tricalcium phosphate $(Ca_3(PO_4)_2)$ or any combination thereof.

In some embodiments the bone graft substitute of the present invention also comprises any one of hydroxyapatite $(Ca_{10})(PO_4)_6(OH)_2)$, hydroxycarbonatedapatite octacalcium phosphate $(Ca_8H_2(PO_4)_6 \cdot 5H_2O)$, Brushite $(CaHPO_4 \cdot 2H_2O)$, monetite $(CaHPO_4)$, fluorapatite $(Ca_{10})(PO_4)_6F_2)$, chlorapatite $(Ca_{10})(PO_4)_6Cl_2)$, Fluorohydroxyapatite $(Ca_{10}(PO_4)_6(OH)_{2-x}F_x)$, tetracalcium phosphate $(Ca_4(PO_4)_2O)$, tricalcium phosphate $(Ca_3(PO_4)_2)$ or any combination thereof.

The molar ratio of Si:metal cation may be between 0.1 and 3, preferably it may be between 0.3 and 2, most preferably between 0.6 and 1.3

The molar ratio of metal cation:phosphate may be between 0.2 and 20, preferably between 5 and 11.

In some embodiments the bone graft substitute of the present invention comprises a silicate based material containing $SiO_2$, CaO and $P_2O_5$.

The molar ratio of $SiO_2$:CaO may be between 0.3 and 2, preferably it may be between 0.6 and 1.3.

The molar ratio of CaO:$P_2O_5$ may be between 0.2 and 20, preferably between 7 and 11.

Density

The bone graft substitutes of the present invention may have a low density.

In some embodiments the density is less than 1.1 $g/cm^3$. Preferably the density is less than 1.0 $g/cm^3$. Preferably the density is less than 0.9 $g/cm^3$. Preferably the density is less than 0.8 $g/cm^3$. Preferably the density is less than 0.7 $g/cm^3$. Preferably the density is less than 0.6 $g/cm^3$. Preferably the density is less than 0.5 $g/cm^3$. Preferably the density is less than 0.4 $g/cm^3$. Preferably the density is less than 0.3 $g/cm^3$. Preferably the density is less than 0.2 $g/cm^3$. Preferably the density is less than 0.18 $g/cm^3$. Preferably the density is less than 0.15 $g/cm^3$.

The density may be from about 1.1 $g/cm^3$ to about 0.001 $g/cm^3$. Preferably the density is from about 1.0 $g/cm^3$ to about 0.001 $g/cm^3$. Preferably the density is from about 0.9 $g/cm^3$ to about 0.001 $g/cm^3$. Preferably the density is from about 0.8 $g/cm^3$ to about 0.001 $g/cm^3$. Preferably the density is from about 0.7 $g/cm^3$ to about 0.001 $g/cm^3$. Preferably the density is from about 0.6 $g/cm^3$ to about 0.001 $g/cm^3$. Preferably the density is from about 0.5 $g/cm^3$ to about 0.001 $g/cm^3$. Preferably the density is from about 0.4 $g/cm^3$ to about 0.001 $g/cm^3$. Preferably the density is from about 0.3 $g/cm^3$ to about 0.001 $g/cm^3$. Preferably the density is from about 1.1 $g/cm^3$ to about 0.01 $g/cm^3$. Preferably the density is from about 1.0 $g/cm^3$ to about 0.01 $g/cm^3$. Preferably the density is from about 0.9 $g/cm^3$ to about 0.01 $g/cm^3$. Preferably the density is from about 0.8 $g/cm^3$ to about 0.01 $g/cm^3$. Preferably the density is from about 0.7 $g/cm^3$ to about 0.01 $g/cm^3$. Preferably the density is from about 0.6 $g/cm^3$ to about 0.01 $g/cm^3$. Preferably the density is from about 0.5 $g/cm^3$ to about 0.01 $g/cm^3$. Preferably the density is from about 0.4 $g/cm^3$ to about 0.01 $g/cm^3$. Preferably the density is from about 0.3 $g/cm^3$ to about 0.01 $g/cm^3$. Preferably the density is from about 1.1 $g/cm^3$ to about 0.1 $g/cm^3$. Preferably the density is from about 1.0 $g/cm^3$ to about 0.1 $g/cm^3$. Preferably the density is from about 0.9 $g/cm^3$ to about 0.1 $g/cm^3$. Preferably the density is from about 0.8 $g/cm^3$ to about 0.1 $g/cm^3$. Preferably the density is from about 0.7 $g/cm^3$ to about 0.1 $g/cm^3$. Preferably the density is from about 0.6 $g/cm^3$ to about 0.1 $g/cm^3$. Preferably the density is from about 0.5 $g/cm^3$ to about 0.1 $g/cm^3$. Preferably the density is from about 0.4 $g/cm^3$ to about 0.1 $g/cm^3$. Preferably the density is from about 0.3 $g/cm^3$ to about 0.1 $g/cm^3$.

Density may be measured by moulding the bone graft substitute into a shape. The volume of the shape can be determined and the sample can be measured to give the density of the bone graft substitute.

Bone graft substitutes with low densities can fill the volume of an implant site but, by weight, use less material. It is expected that with less material to resorb, resorption will occur faster. A higher density bone graft substitute is expected to take longer to resorb.

Then density of the bone graft substitutes of the present invention can be tailored by varying the relative amounts of solvent used during gel formation.

The ability to control the density of the material therefore gives control over the resorption rate, allowing for the development of tailored compositions to meet clinical requirements.

The low densities of the bone graft substitutes of the present invention reduces the problematic build-up of high pH around the implant site.

Without wishing to be bound by theory, the bone graft substitutes of the present invention use significantly less material by weight to fill a given volume and there is consequently insufficient volume of material present to raise pH to a problematic level.

Pore Diameter

The bone graft substitutes of the present invention may have average pore diameters that are typical of a mesoporous material.

In some embodiments the average pore diameter of the bone graft substitute may be from about 1 to about 99 nm. It may be from about 1 to about 70 nm. It may be from about 1 to about 50 nm. It may be from about 1 to about 25 nm. It may be from about 1 to about 20 nm. It may be from about 1 to about 18 nm. It may be from about 5 to about 99 nm. It may be from about 5 to about 70 nm. It may be from about 5 to about 50 nm. It may be from about 5 to about 25 nm. It may be from about 5 to about 20 nm. It may be from about 5 to about 18 nm. It may be from about 10 to about 99 nm. It may be from about 10 to about 70 nm. It may be from about 10 to about 50 nm. It may be from about 10 to about 25 nm. It may be from about 10 to about 20 nm. It may be from about 10 to about 20 nm. It may be from about 10 to about 18 nm. It may be from about 14 to about 99 nm. It may be from about 14 to about 70 nm. It may be from about 14 to about 50 nm. It may be from about 14 to about 25 nm. It may be from about 14 to about 20 nm. It may be from about 14 to about 20 nm. It may be from about 14 to about 18 nm.

Increased pore diameter is associated with increased porosity and pore volume. This allows more body fluid to enter the bone graft substitute and contact a surface of the bone graft substitute which may increase the rate of precipitation of apatite.

The average pore diameter is measured using $N_2$ adsorption via the non-local density functional theory (NLDFT) method.

Non-local density functional theory aims to explain the experimental isotherms observed when gas molecules are adsorbed on a solid surface and serves as the basis for an important analysis technique for the measurement of the specific surface area and porosity of a material. For a more detailed description of the theory and method see J Landers et al., "Density functional theory methods for characterization of porous materials", *Colloids and Surfaces A: Physicochemical and Engineering Aspects*, 2013, vol 437, page 3-32.

Pore Volume

The bone graft substitutes of the present invention may have a high average pore volume. The term average pore volume as used herein refers to the median average pore volume.

In some embodiments the average pore volume of the bone graft substitute may be from about 1 to about 20 cm$^3$/g. It may be from about 1 to about 10 cm$^3$/g. It may be from about 1 to about 8 cm$^3$/g. It may be from about 2 to about 20 cm$^3$/g. It may be from about 2 to about 10 cm$^3$/g. It may be from about 2 to about 8 cm$^3$/g. It may be from about 3.5 to about 20 cm$^3$/g. It may be from about 3.5 to about 10 cm$^3$/g. It may be from about 3.5 to about 8 cm$^3$/g. It may be from about 4 to about 20 cm$^3$/g. It may be from about 4 to about 10 cm$^3$/g. It may be from about 4 to about 8 cm$^3$/g. It may be greater than about 2 cm$^3$/g. It may be greater than about 3 cm$^3$/g. It may be greater than about 4 cm$^3$/g.

The high average pore volume contributes to the reduced remodelling time of the bone graft substitutes of the present invention.

The average pore volume is measured using $N_2$ adsorption via the non-local density functional theory (NLDFT) method.

Surface Area

The bone graft substitutes of the present invention may have a high surface area.

In some embodiments the surface area is greater than 400 m$^2$/g. Preferably the surface area is greater than 450 m$^2$/g. Preferably the surface area is greater than 500 m$^2$/g. Preferably the surface area is greater than 550 m$^2$/g. Preferably the surface area is greater than 600 m$^2$/g. Preferably the surface area is greater than 650 m$^2$/g. Preferably the surface area is greater than 700 m$^2$/g. Preferably the surface area is greater than 750 m$^2$/g. Preferably the surface area is greater than 800 m$^2$/g. Preferably the surface area is greater than 850 m$^2$/g. Preferably the surface area is greater than 860 m$^2$/g. Preferably the surface area is greater than 870 m$^2$/g. Preferably the surface area is greater than 880 m$^2$/g.

The surface area may be measured using $N_2$ adsorption via the Brunauer Emmett Teller (BET) method. Brunauer-Emmett-Teller (BET) theory aims to explain the physical adsorption of gas molecules on a solid surface and serves as the basis for an important analysis technique for the measurement of the specific surface area and porosity of a material. For a more detailed description of the theory and method see S. Brunauer, P. H. Emmett, E. Teller, Journal of the American Chemical Society, 1938, 60(2), page 309-319.

Bone graft substitutes of the present invention achieve very high surface areas (~850 m$^2$/g), significantly higher than bioactive glasses. This gives proteins and cells a larger surface to attach to, contributing to high osseointegration and rapid resorption.

Other Features

In some embodiments the bone graft substitutes of the present invention are bioactive.

Preferably, the bone graft substitute of the present invention is a bioactive aerogel or a bioactive cryogel.

In this regard the term bioactive is used to describe materials that exhibit the ability to form any one of hydroxyapatite $(Ca_{10})(PO_4)_6(OH)_2)$, hydroxycarbonatedapatite octacalcium phosphate $(Ca_8H_2(PO_4)_6 \cdot 5H_2O)$, Brushite $(CaHPO_4 \cdot 2H_2O)$, monetite $(CaHPO_4)$, fluorapatite $(Ca_{10})(PO_4)_6F_2)$, chlorapatite $(Ca_{10})(PO_4)Cl_2 2)$, Fluorohydroxyapatite $(Ca_{10}(PO_4)_6(OH)_{2-x}F_x)$ or a mixture of any of these on its surface when submerged in an aqueous solution such as a simulated body fluid solution.

A simulated body fluid is a solution with an ion concentration close to that of human blood plasma, kept under mild conditions of pH and identical physiological temperature. A simulated body fluid may be prepared using a known method. For example the simulated body fluid may be made according to the procedure of Kokubo et al. (Journal of Biomedical Materials Research, 1990, 24, pp 721-734).

The bioactivity of a material may be measured using an industry standard test comprising the steps of contacting the material with simulated body fluid and monitoring the absorption spectra of the material by infra-red spectroscopy. For example, in the case of hydroxyapatite deposition two absorbance peaks at around 560 cm$^{-1}$ and 600 cm$^{-1}$ respectively are observed.

The bone graft substitutes of the present invention may exhibit the formation of apatite in less than 24 hours after submersion in a simulated body fluid solution. For example, apatite may be formed in less than 15 hours. For example, apatite may be formed in less than 5 hours.

Preferably the bone graft substitutes of the present invention do not require surface activation in order to exhibit bioactivity. Without wishing to be bound by theory, it is thought that surface treatment of bone graft substitutes of the present invention would result in the precipitation of the metal cations and, if present, the phosphate from within the silicate network. This precipitation may occur spontaneously without the need for contacting a body fluid or simulated body fluid resulting in precipitation before, for example, implantation into a subject.

The nature of the bone graft substitutes of the present invention mean they may be moulded to desired dimensions without cracking. Bone graft substitutes of the present invention could therefore be moulded to the shape required in any clinical situation.

Whilst melt-quench derived bioactive glasses can be cast into shapes during pouring, the shape and size is very limited due to the propensity of these glasses to crystallise when cooled too slowly.

Additionally such poured glasses would have a very low surface areas resulting in very long remodelling rates.

Bone graft substitutes of the present invention are silicate based. Silicate based bioactive materials have been shown to exhibit high rates of osseointegration. The bone graft substitutes of the present invention also have a high surface area.

These features give bone graft substitutes of the present invention a number of favourable properties.

The bone graft substitute may contain a fluoride, the fluoride content expressed as a divalent or monovalent fluoride being up to 25 mole percent, preferably up to 18 mole percent, more preferably between 0.01 and 12 mole percent, most preferably between 0.01 and 5 mole percent.

The bone graft substitute may contain a metal fluoride.

Fluoride addition is beneficial because it should promote the formation of fluoroapatite. Fluoroapatite is more resistant to acid dissolution in oral fluids than hydroxyapatite and aids in the prevention of dental decay. Moreover, fluoride ions are known to aid apatite formation and stimulate the cell division of osteoblasts, the bone forming cells.

The bone graft substitute of the present invention may contain strontium.

The addition of strontium may provide further beneficial properties to the bone graft substitutes of the present invention. Strontium has been shown to promote bone formation by inhibiting osteoclasts and promoting osteoblasts making it desirable in conditions where bone is weak i.e. osteoporosis. Strontium may also add a degree of radiopacity to cements, which is a favourable property allowing the implanted bone graft substitute to be observed radiographically by X-rays and enables the surgeon to follow resorption of the cement or implant.

The bone graft substitute of the present invention may contain zinc.

The addition of zinc may provide further beneficial properties to the bone graft substitutes of the present invention. For example, it has been shown that, in small quantities, zinc significantly increases proliferation of human osteoblastic cells. Additionally, it is thought that could promote healing because zinc is a cofactor in many enzymes in the body which affect healing times.

The bone graft substitute of the present invention may contain cobalt. Cobalt has been shown to induce angiogenesis.

Fillers may be added to the composition to improve radio-opacity for visualisation by X-rays. The fillers may include species based on high atomic number elements defined here as: Z>40 to include oxides, carbonates and phosphates of Sr, Ba, Zn, Zr and Bi.

The bone graft substitute of the present invention may be granular, for example the bone graft substitute may formed of sub-millimetre porous granules. Preferably the bone graft substitute is formed of porous granules from 200-800 μm in size.

Bone Graft Substitute Preparation

A further aspect of the present invention is a process of making a bone graft substitute comprising; a gel formation stage; a gel drying stage and a calcination stage.

The gel formation stage comprises the steps of dissolving a metal cation in a first solvent, adding a silicate to the first solvent and gelling of the resultant mixture. Preferably a phosphate is also dissolved in the first solvent before adding a silicate.

In some embodiments the gel formation stage includes the step of adding any one of hydroxyapatite ($Ca_{10}(PO_4)_6(OH)_2$), hydroxycarbonatedapatite octacalcium phosphate ($Ca_8H_2(PO_4)_6 \cdot 5H_2O$), Brushite ($CaHPO_4 \cdot 2H_2O$), monetite ($CaHPO_4$), fluorapatite ($Ca_{10}(PO_4)_6F_2$), chlorapatite ($Ca_{10}(PO_4)_6Cl_2$), Fluorohydroxyapatite ($Ca_{10}(PO_4)_6(OH)_{2-x}F_x$), tetracalcium phosphate ($Ca_4(PO_4)_2O$), tricalcium phosphate ($Ca_3(PO_4)_2$) or any combination thereof to the first solvent.

In some embodiments the first solvent is an aqueous solvent, for example it may be $H_2O$, for example it may be an aqueous solution, for example it may be an aqueous solution having a molarity between 0.1-0.2M.

In some embodiments the aqueous solution contains fluoride anions. Preferably the aqueous solution contains sodium fluoride, for example it may be an aqueous solution of sodium fluoride having a molarity between 0.1-0.2M.

In some embodiments the aqueous solution is a basic solution, for example the aqueous solution may be a basic solution containing fluoride ions.

Alternatively in some embodiments the solution is mildly acidic, preferably having a pH between 6 and 7. For example the aqueous solution may be a mildly acidic solution containing fluoride ions. Without wishing to be bound by theory, it is thought that more acidic aqueous solutions (with pH less than 6) may result in the precipitation of the silicate and prevent the formation of a gel.

In some embodiments the molar ratios of aqueous solution to silicate is between 25:1 and 10:1. For example it may be between 25:1 and 12:1. It may be between 25:1 and 12:1. It may be between 25:1 and 15:1. It may be between 25:1 and 16:1. It may be between 20:1 and 10:1. It may be between 20:1 and 12:1. It may be between 20:1 and 15:1. It may be between 20:1 and 16:1. It may be between 18:1 and 10:1. It may be between 18:1 and 12:1. It may be between 18:1 and 15:1. It may be between 18:1 and 16:1. For example, it may be around 17:1.

In some embodiments the metal cation is selected from a calcium cation, a strontium cation, a sodium cation, a zinc cation, a magnesium cation, a potassium cation, a titanium cation, a cobalt cation, an aluminium cation or a silver cation. Optionally, the metal cation is selected from a calcium cation, a strontium cation or a sodium cation. Preferably the metal cation is a calcium cation. It may be that only one metal cation is present or it may be that a mixture of two or more metal cations is present.

In some embodiments the metal cation is provided by a metal salt.

In some embodiments the metal cation is provided by a calcium salt. Preferably the calcium salt is selected from calcium nitrate tetrahydrate, calcium acetate and calcium nitrate.

In some embodiments the metal cation is provided in whole or in part by any one of hydroxyapatite ($Ca_{10}(PO_4)_6(OH)_2$), hydroxycarbonatedapatite octacalcium phosphate ($Ca_8H_2(PO_4)_6 \cdot 5H_2O$), Brushite ($CaHPO_4 \cdot 2H_2O$), monetite ($CaHPO_4$), fluorapatite ($Ca_{10}(PO_4)_6F_2$), chlorapatite ($Ca_{10}(PO_4)_6Cl_2$), Fluorohydroxyapatite ($Ca_{10}(PO_4)_6(OH)_{2-x}F_x$), tetracalcium phosphate ($Ca_4(PO_4)_2O$), tricalcium phosphate ($Ca_3(PO_4)_2$) or any combination thereof.

In some embodiments the phosphate is provided by triethylphosphate.

In some embodiments the phosphate is provided in whole or in part by any one of hydroxyapatite ($Ca_{10}(PO_4)_6(OH)_2$), hydroxycarbonatedapatite octacalcium phosphate ($Ca_8H_2(PO_4)_6 \cdot 5H_2O$), Brushite ($CaHPO_4 \cdot 2H_2O$), monetite ($CaHPO_4$), fluorapatite ($Ca_{10}(PO_4)_6F_2$), chlorapatite ($Ca_{10}(PO_4)_6Cl_2$), Fluorohydroxyapatite ($Ca_{10}(PO_4)_6(OH)_{2-x}F_x$), tetracalcium phosphate ($Ca_4(PO_4)_2O$), tricalcium phosphate ($Ca_3(PO_4)_2$) or any combination thereof.

In some embodiments the silicate is selected from tetraethyl orthosilicate (TEOS), waterglass or tetramethyl orthosilicate (TMOS). Preferably the silicate is tetraethyl orthosilicate.

The gel formation stage results in a gel having a liquid dispersed phase.

In some embodiments the gel formation stage further comprises a liquid phase replacement stage.

The liquid phase replacement stage comprises the step of soaking the gel in the second solvent. The liquid phase replacement stage may comprise a plurality of soaking phases.

For example, the gel may be soaked in a mixture of the liquid phase and second solvent for a time period followed by subsequently soaking in a mixture of the liquid phase and second solvent having a greater proportion of the second solvent for a time period.

The second solvent may be an organic solvent, preferably it may be an alcohol, more preferably it may be ethanol.

For example, the gel may be soaked in 60% ethanol for around 24 hours, followed by optionally soaking in 80% ethanol for around 24 hours and followed by optionally soaking in 95% ethanol for around 24 hours. Finally the gel may be soaked in 100% ethanol for around 24 hours.

In some embodiments the molar ratios of the second solvent to silicate is between 25:1 and 10:1. For example it may be between 25:1 and 12:1. It may be between 25:1 and 12:1. It may be between 25:1 and 15:1. It may be between 25:1 and 16:1. It may be between 20:1 and 10:1. It may be between 20:1 and 12:1. It may be between 20:1 and 15:1. It may be between 20:1 and 16:1. It may be between 18:1 and 10:1. It may be between 18:1 and 12:1. It may be between 18:1 and 15:1. It may be between 18:1 and 16:1. For example, it may be around 17:1. It may be the molar ratio is the molar ratio used for each wash. It may be the molar ratio is the molar ratio used for all washes combined.

The liquid phase replacement stage results in the liquid phase of the gel produced in the gelling step being replaced with a second solvent. The second solvent is then the liquid phase of the gel.

The gel drying stage may be carried out by freeze-drying, supercritical drying or subcritical drying. Preferably the gel drying stage is carried out by freeze-drying or supercritical drying. In some embodiments the gel drying stage is carried out by supercritical drying in liquid $CO_2$.

The term supercritical drying is used herein to refer to a process that removes liquid in a precise and controlled way and is well known in the field. Without wishing to be bound by theory, supercritical drying refers to a process whereby the liquid to be removed does not cross a phase boundary.

Supercritical drying may be carried out using the CPD method using a Tousimis 931 critical point dryer. The samples may be subjected to three stasis cycles, each stasis cycle being around 8 hours.

The term freeze-drying is used herein to refer to a process that removes liquid in a precise and controlled way and is well known in the field. Freeze-drying is also commonly known as lyophilisation or cryodesiccation. Without wishing to be bound by theory, freeze-drying works by freezing the material and then reducing the surrounding pressure to allow the frozen liquid in the material to sublimate directly from the solid phase to the gas phase.

Freeze-drying may be carried out by using a VirTis AdVantage Plus benchtop Freeze Dryer. The gel may be immersed in either tert-butanol or deionised water for 24 hours. This step may be repeated a minimum of three times. The gels may then be frozen in liquid nitrogen after which they are transferred to the freeze drier.

The term subcritical drying is used herein to refer to a process of surface modifying the gel before drying at non-supercritical pressures, for example at ambient pressure. Without wishing to be bound by theory the presence of surface modifying groups on the internal surface of the pores in combination with the solvent of the liquid phase of the gel results in a low capillary pressure during the drying.

Surface modification may be carried by treating the gel with a surface modifying agent such as trimethylchlorosilane. Subsequently, drying of the gel can be carried out at ambient pressure at room temperature followed by 24 hours at 323 K and 24 hours at 373 K.

The gel drying stage results in the liquid phase of the gel produced in the gel formation stage being replaced with a gaseous phase.

Without wishing to be bound by theory, replacing the liquid phase with a gaseous phase maintains the structure of the solid phase of the gel and results in a low density, highly porous material.

The calcination stage comprises the step of heating the dried gel.

The calcination stage may be carried out at a temperature of at least 400 K, for example at least 450 K, for example at least 500 K, for example at least 550 K, for example at least 600 K, for example at least 650 K. The calcination step may be carried out at a temperature less than 1000 K, for example less than 900 K, for example less than 800 K.

The calcination stage may be carried out for at least 1 hour, for example at least 2 hours, for example at least 3 hours.

The calcination stage results in the incorporation of metal cations and, if present, phosphate into the silicate structure.

The bones graft substitutes of the present invention are similar in composition to bioactive glasses and, like bioactive glasses, form hydroxyapatite or carbonate substituted apatite, giving them many of the same beneficial properties for bone grafting. However, the low and controllable density of the bones graft substitutes of the present invention addresses the remodelling rate and pH issues experienced that are experienced with other bones graft substitutes such as bioactive glasses.

For example, the drying stage enables the low density structure and porosity to be maintained. The present invention provides the ability, via changes in the synthesis methods, to alter the density of the material from 1.1 g cm$^{-3}$ to 0.05 g cm$^{-3}$. In particular, changes to the solvent(s) which make up the liquid dispersed phase of the gel (prior to the drying stage) results in different pore sizes and dispersion in the gel.

Further Aspects

A further aspect of the present invention provides a bone graft substitute obtainable by a process comprising a gel formation stage; a gel drying stage and a calcination stage. The process may comprise any of the features as outlined above.

A further aspect of the invention provides for a granular composition of the bone graft substitute of the present invention. In some embodiments the granules are sub-millimetre sized porous granules. Preferably the granular composition is formed of porous granules from 200-800 μm in size.

A further aspect of the invention provides a composition comprising the bone graft substitutes of the present invention and at least one other biomaterial. In some embodiments the bone graft substitute of the present invention is a filler. Preferably the bone graft substitute is bioactive. In this way the bone graft substitute may impart bioactivity on the composition.

For example the composition may comprise PMMA and a bone graft substitute of the present invention. The bone graft substitute may be a bioactive gel, for example a bioactive aerogel. The bone graft substitute may be dispersed in the PMMA matrix as a filler.

In some embodiments, the composition is a cement. For example the composition may be similar to PMMA-bioglass cements that are currently used for kyphoplasty.

In some embodiments the at least one biomaterial may comprise hydroxyapatite ($Ca_{10}(PO_4)_6(OH)_2$), hydroxycarbonatedapatite octacalcium phosphate ($Ca_8H_2(PO_4)_6 \cdot 5H_2O$), Brushite ($CaHPO_4 \cdot 2H_2O$), monetite ($CaHPO_4$), fluorapatite ($Ca_{10}(PO_4)_6F_2$), chlorapatite ($Ca_{10}(PO_4)_6Cl_2$), Fluorohydroxyapatite ($Ca_{10}(PO_4)_6(OH)_{2-x}F_x$), tetracalcium phosphate ($Ca_4(PO_4)_2O$), tricalcium phosphate ($Ca_3(PO_4)_2$) or any combination thereof.

A further aspect of the invention provides a method of treatment or surgery comprising inserting a bone graft substitute of the present invention into a subject.

In some embodiments the bone graft substitute is implanted into the subject. For example, the bone graft substitute may be implanted into a tooth socket following extraction or implanted into an orthopaedic bone site during surgery.

In some embodiments the bone graft substitute is injected into the subject. For example, the bone graft substitute may be injected into the site of a bone fracture.

In some embodiments the bone graft substitute is mixed with fluid extracted from the subject before implantation.

Methods of treatment or surgery include restorative filling of teeth or the roots of teeth, replacing alveolar bone, injection in the treatment of osteoporotic fractures of the vertebrae including vertebroplasty, kyphoplasty, spinal fusion procedures, treatment of bone cancers, joint replacement surgery and orthopaedic trauma.

A further aspect of the invention provides a method of promoting bone growth by treating a bone graft substitute of the present invention under physiological conditions.

In some embodiments the promotion of bone growth is carried out in vivo, for example by implanting a bone graft substitute of the present invention into a subject.

In some embodiments the promotion of bone growth is carried out in vitro, for example by treating a bone graft substitute of the present invention with a simulated body fluid or fluid extracted from a subject.

In a further aspect of the invention the bone graft substitutes of the invention are used in dental medical or oral healthcare applications.

In some embodiments the bone graft substitute of the present invention is used as a dental implant. The bone graft substitute may be implanted into a tooth socket, for example immediately after extraction or loss of the tooth. The bone graft substitute may be mixed with fluid extracted from the subject prior to implantation.

In some embodiments the bone graft substitute is used as an orthopaedic implant. The bone graft substitute may be injected or implanted into the subject, for example the bone graft substitute may be injected into a subject at the site of a fracture or other bone loss (e.g. congenital or disease related). The bone graft substitute may be mixed with fluid extracted from the subject prior to implantation.

Possible uses include, but are not limited to, a restorative dental bone graft for filling teeth or the roots of teeth, replacing/regenerating alveolar bone, for injection in the treatment of osteoporotic fractures of the vertebrae including vertebroplasty, kyphoplasty, for use in spinal fusion procedures, treatment of bone cancers and bone augmentation procedures during joint replacement surgery and orthopaedic trauma cases.

In some embodiments the bone graft substitute of the present invention is used in oral healthcare. The bone graft substitute may be incorporated into a toothpaste or chewing gum. In this way the bone graft substitute may facilitate remineralisation of tooth enamel or precipitation of hydroxyapatite or carbonate substituted apatite on the surface of the tooth or within the tooth enamel or within the dentinal tubules.

A further aspect of the invention provides use of the bone graft substitutes of the invention in combination with other bioactive materials. In some embodiments the bone graft substitute of the present invention is used as a filler. Preferably the bone graft substitute is bioactive. In this way the bone graft substitute may impart bioactivity on the combination of bone graft substitute and other bioactive material.

In another aspect of the present invention the bone graft substitutes of the present invention are used as vehicles for drug delivery.

In some embodiments the drug is adsorbed into the bone graft substitute. In some embodiments the bone graft substitute is bonded to the drug, for example, it may be bonded covalently or ionically.

The advantages of using bone graft substitutes as a vehicle for drug delivery include delivery of the drug to the site at which it is intended to have its effect, for instance antibiotic drugs can be added to prevent post-surgical infections. Delivering the drug to the site of intended effect reduces the quantity of drug that would have had to be administered if the drug were administered orally or intravenously.

In respect of each of the possible therapeutic or surgical methods, uses, and utilities practised on the human or animal body described above, there is also provided:

Use of the materials (bone graft substitutes, or the constituents of their manufacture) in the preparation of a medicament or implant or filler) for use in that therapeutic or surgical context, The material (bone graft substitute) for use as a medicament or implant or filler in that therapeutic or surgical context.

DEFINITION OF TERMS

Throughout this specification, including the claims which follow, unless the context requires otherwise, the word "comprise" and variations such as "comprises" and "comprising," will be understood to imply the inclusion of a stated integer or step or group of integers or steps but not the exclusion of any other integer or step or group of integers or steps.

Where a material described herein is disclosed as comprising or including a specified mixture of components, it will be understood that there is likewise disclosed mutatis mutandis a material "consisting" of those components, or "consisting essentially" of those components.

It must be noted that, as used in the specification and the appended claims, the singular forms "a," "an," and "the" include plural referents unless the context clearly dictates otherwise. Thus, for example, reference to "a drying step" includes combinations of two or more such drying steps, and the like.

Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

The term remodelling is used herein to refer to the process of resorption and replacement of the bone graft substitute material with native bone.

The term resorption is used herein to refer to the process of absorbing the graft material into the subject body.

The term replacement is used herein to refer to the process of replacing graft material with new native bone.

The term osseointegration is used herein to refer to the integration of native bone and bone graft substitute material.

The term osteoconduction is used herein to refer the ability of a bone graft substitute material to provide a conductive lattice for native bone growth.

The term osteoinduction is used herein to refer the ability of a bone graft substitute material to recruit host stem cells, such as mesenchymal stem cells, from the surrounding tissue of the host, which then differentiate into osteoblastic cells.

The term silicate is used herein to refer to substances containing a silicon atom. Strictly, the silicon atom is in the structure as an ion and not as a neutral atom. The silicon atom is, however, commonly associated with oxygen. For example, the silicon atom may be in the form of an $SiO_4^{4-}$ ions or an $SiO_2$ unit.

The term phosphate is used herein to refer to substances containing at least one phosphorus atom covalently bonded to one or more oxygen atoms. The phosphate may be derived from phosphoric acid. In particular it may be derived from salts of phosphoric acid, anhydrides of phosphoric acid, esters of phosphoric acid and combinations thereof.

The phosphate may be negatively charged or neutral.

The term subject is used herein to refer to a human or animal patient.

Headings and sub-headings used throughout this specification are for information only.

EMBODIMENTS OF THE INVENTION AND EXPERIMENTAL DATA

Figure 1:
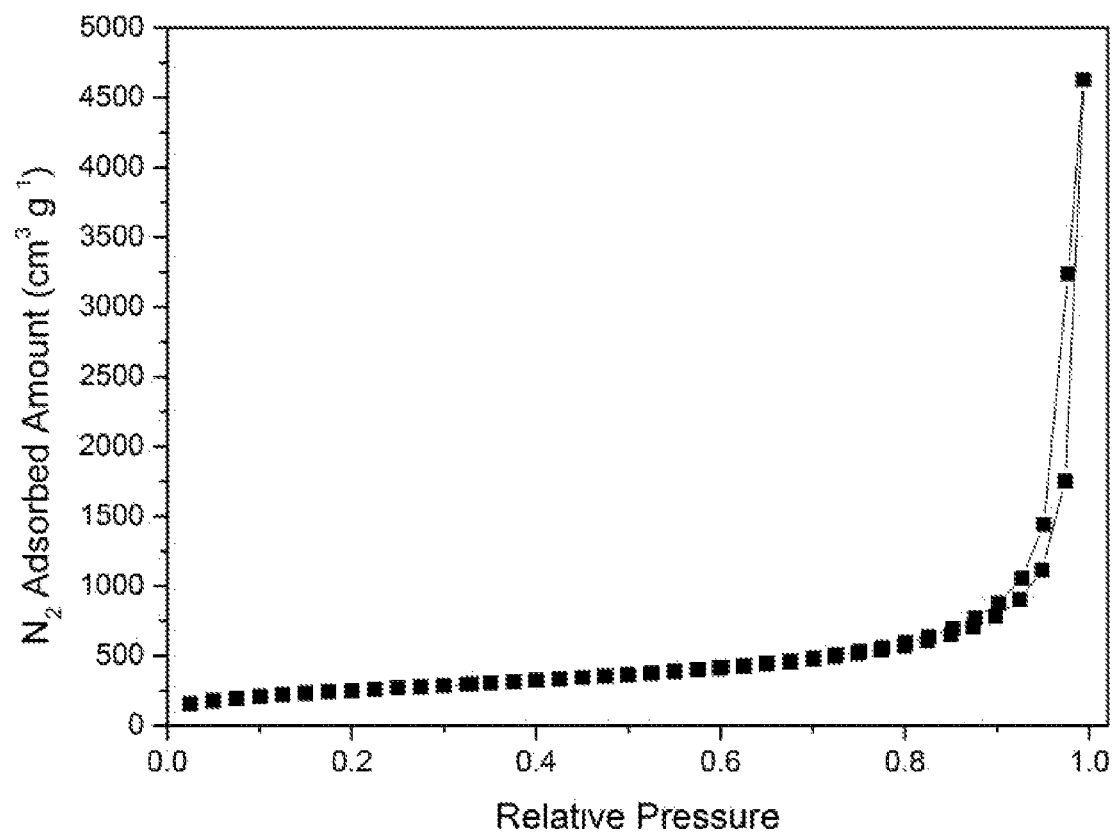
FIG. 1: Shows a graph of the $N_2$ adsorption and description isotherm of Sample 2.

The present invention is now illustrated with reference to the following non-limiting examples and accompanying figures.

Example 1

Example 1 describes a method used to produce bone graft substitutes of the present invention.

Reagents
0.14M NaF solution
Absolute (100%) ethanol
tetraethyl orthosilicate (TEOS, $(Si(OC_2H_5)_4)$)
Calcium nitrate tetrahydrate $(Ca(NO_3)_2 \cdot 4H_2O)$
Triethyl phosphate $((C_2H_5)_3PO_4)$ Calcium nitrate tetrahydrate was dissolved in 0.14 M solution of NaF, after which ethanol was added. This mixture was then stirred for 5 minutes and then triethyl phosphate $((C_2H_5)_3PO_4)$ added.

Finally the TEOS was combined slowly with this solution and allowed to stir for thirty seconds.

4 ml of the solution was cast into cylindrical moulds (Ø11 mm×50 mm height, via syringe). Each mould was then covered with film and placed into glass container.

Each sample was then gelled for 48 hours at 60° C.

Each sample was then placed into 60% ethanol. After 24 hours the solution was changed for 80% ethanol. After another 24 hours it was changed once again for 95% ethanol. Finally the solution was replaced with 100% ethanol.

Each sample was dried using the CPD method using a Tousimis® 931 critical point drier. Each sample was run through three stasis cycles of eight hours each.

After critical drying each sample was then calcined at 700° C. for three hours.

Example 2

Six samples were prepared using the method of example 1. Table 1 shows the chemical composition and density of samples 1-6.

All samples were produced with the following molar ratios of $H_2O$, ethanol and TEOS of 17.26:16.71:1.00.

TABLE 1

| | Chemical compositions | | | |
|---|---|---|---|---|
| Composition | $SiO_2$ (mol %) | $P_2O_5$ (mol %) | CaO (mol %) | Density (g cm$^{-3}$) |
| Sample 1 | 38.00 | 6.00 | 56.00 | 0.126 |
| Sample 2 | 40.00 | 6.00 | 54.00 | 0.190 |
| Sample 3 | 42.25 | 6.00 | 51.75 | Not determined |
| Sample 4 | 44.69 | 6.00 | 49.31 | 0.122 |
| Sample 5 | 47.50 | 6.00 | 46.50 | 0.248 |
| Sample 6 | 50.80 | 6.00 | 43.20 | 0.132 |

The data presented in table 1 shows both the compositions of and densities of five compositions of bioactive aerogels.

This data demonstrates the ability to produce a range of compositions. It is also clear that very low densities can be achieved for the bone graft substitutes of the present invention.

Density is an important property for bone graft substitutes. The ability to produce bone graft substitutes having low densities represents one of the key advantages of the present invention.

Bone graft substitutes with low densities may provide rapid remodelling times and significantly reduce any potential pH rise associated with the ion exchange processes.

Example 3

Further analysis of sample 2 was conducted, and key properties measured. These are set out in Table 2 below. The average pore diameter and pore volume were obtained from $N_2$ adsorption using the NLDFT method. The surface area was obtained from $N_2$ adsorption using the BET method. The density was measure by calculating the volume of the sample and weighing the sample.

Sample 2 was produced according to the method outlined in example 1.

TABLE 2

Key properties of Sample 2

| Property | Value |
| --- | --- |
| Density | 0.19 g cm$^{-3}$ |
| Average Pore Diameter | 16.0 nm |
| Surface Area | 892 m$^2$ g$^{-1}$ |
| Pore Volume | 4.92 cm$^3$ g$^{-1}$ |

Table 2 shows a number of properties of sample 2 measured using $N_2$ adsorption analysis. This data supports the previous data showing low densities and confirms pores in the nm scale and a high pore volume.

Current sol-gel glasses used as bone graft materials have a maximum surface area of around 450 m$^2$ g$^{-1}$. The data for sample 2 show that bone graft substitutes of the present invention can have a surface area of nearly double the maximum of currently used bone graft substitutes.

The surface area data show another advantage of the bone graft substitutes of the present invention. It has been shown that the high surface areas of silicate based bone graft substitutes lead to superior in-vivo performance.

Without wishing to be bound by theory it is proposed that the higher surface area allows for improved adhesion of proteins and cells that are involved with osseointegration and remodelling.

Example 4

FIG. 1 shows the $N_2$ adsorption isotherm of sample 2.

Bioactivity testing (ability to precipitate hydroxyapatite) was carried out on sample 2 using a simulated body fluid test.

Figure 2:
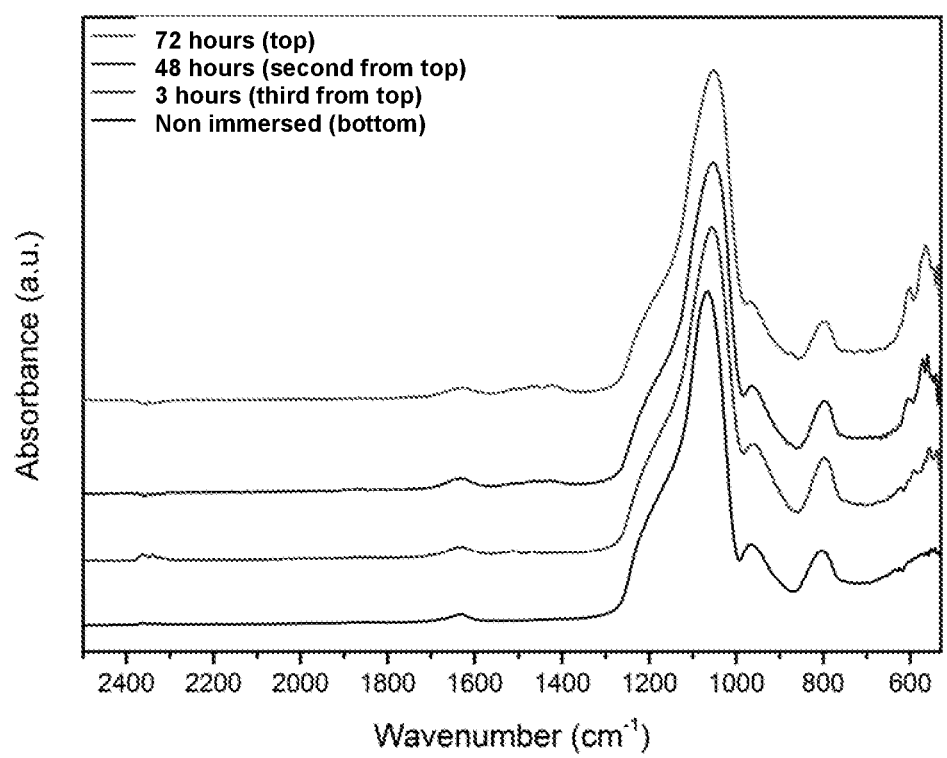
FIG. 2: Shows the FTIR analysis of Sample 2 when treated with simulated body fluids.

FIG. 2 shows the absorbance spectra after 3 hours of immersion in simulated body fluid. The precipitation of hydroxyapatite is confirmed by the presence of two bands at 560 and 600 cm$^{-1}$.

This is an industry standard test to demonstrate that a material is bioactive. This test is widely accepted to demonstrate that a material which is bioactive in simulated body fluid would, once in the body, be able to form bone on its surface. This is an essential property for bone substitute materials.

Figure 3:
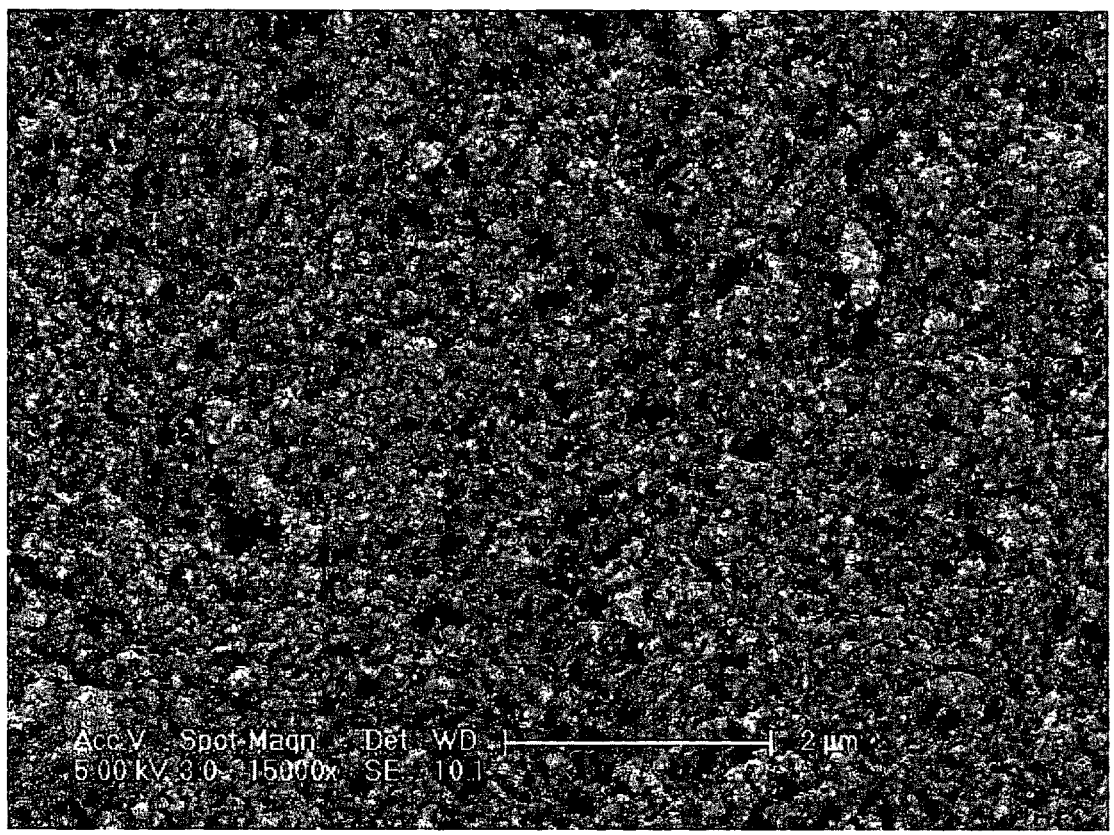
FIG. 3: Shows a scanning electron micrograph of Sample 2 after calcination.
Figure 4:
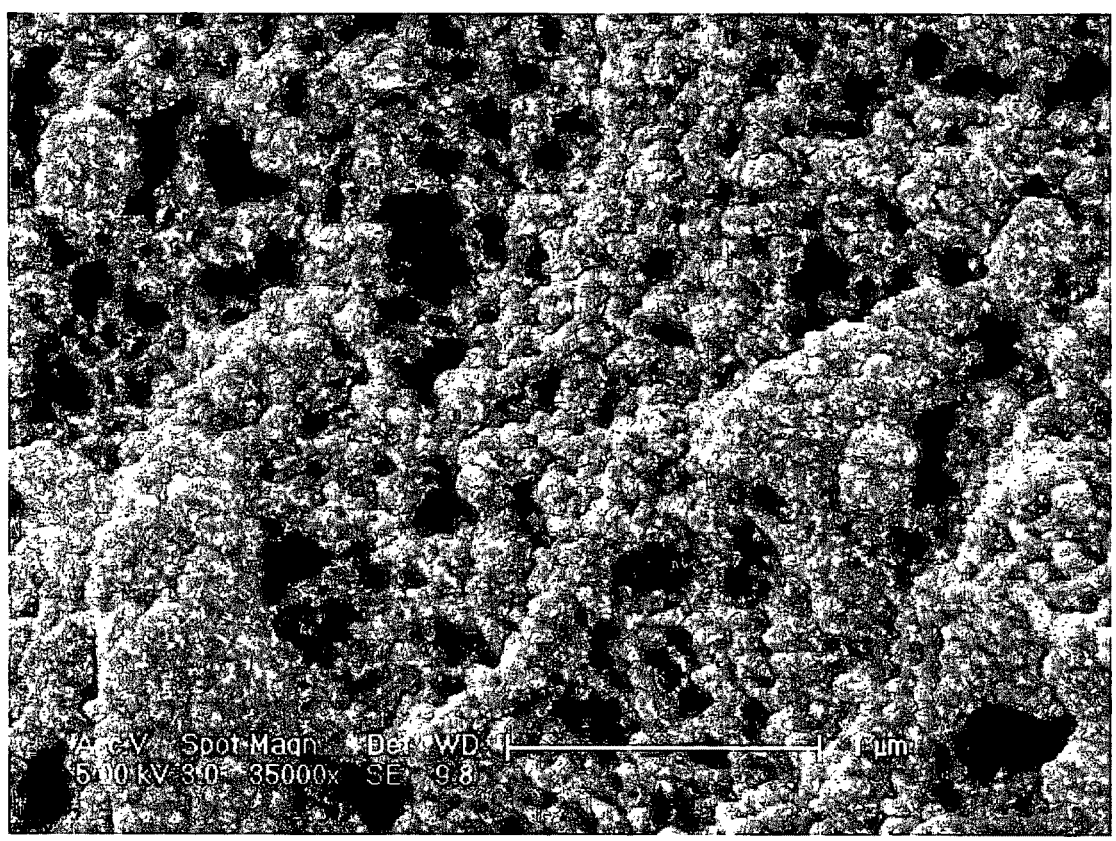
FIG. 4: Shows a zoomed in scanning electron micrograph of Sample 2 after calcination.
Figure 5:
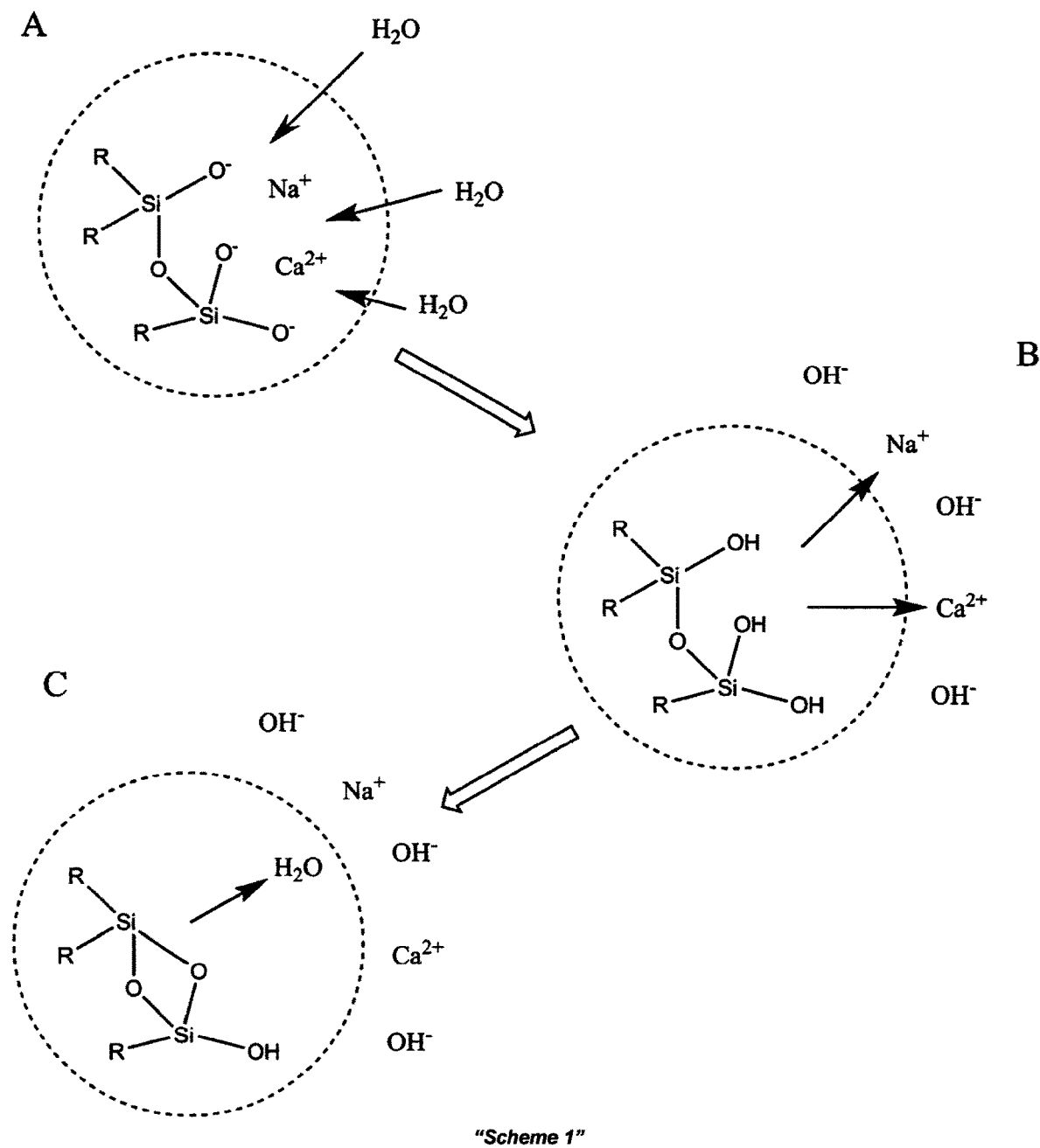
FIG. 5: Shows scheme 1.
Figure 6:
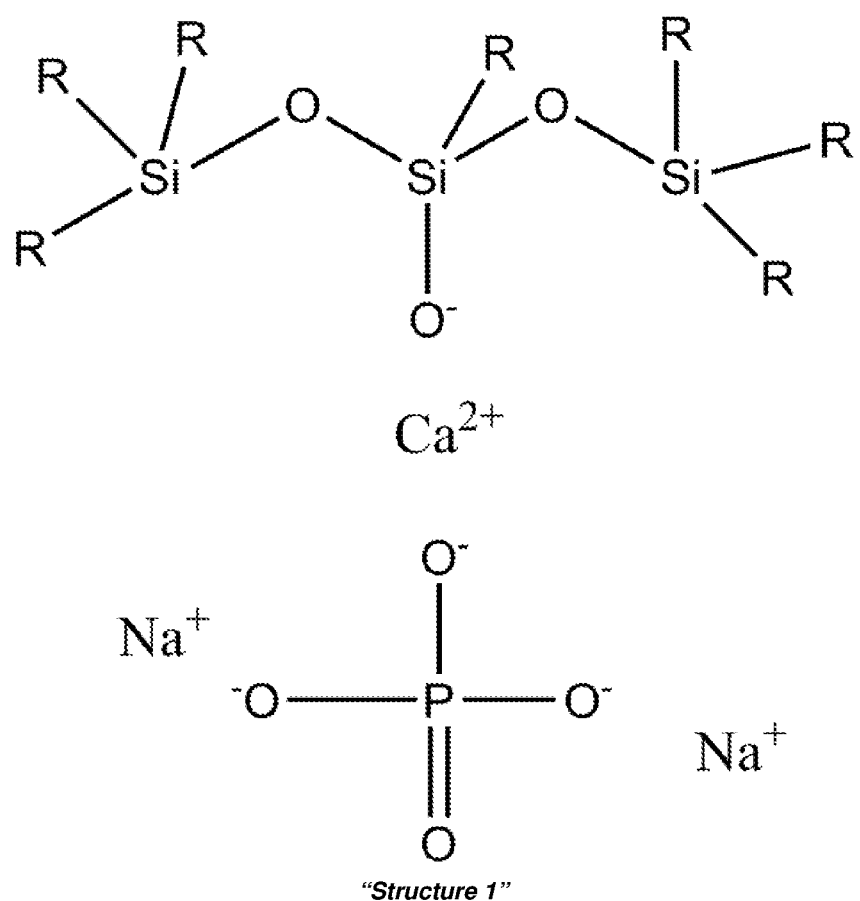
FIG. 6: Shows structure 1.
Figure 7:
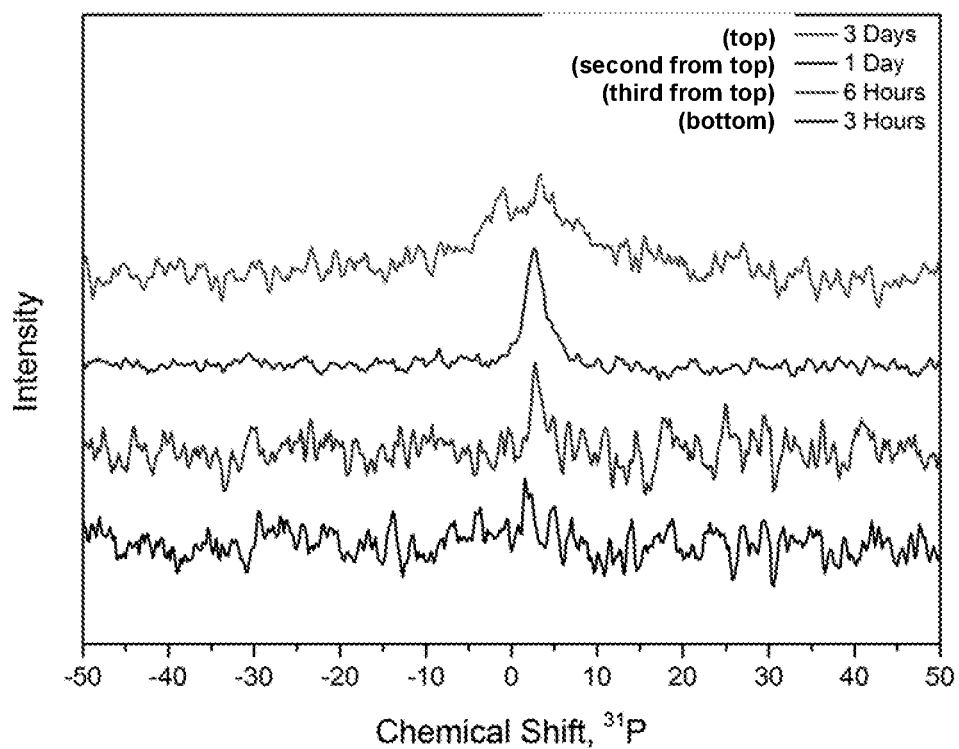
FIG. 7: Shows the $^{31}P$ NMR spectra of Sample 1 after 3 hours, 6 hours, 1 day, 3 days immersion in SBF solution.
Figure 8:
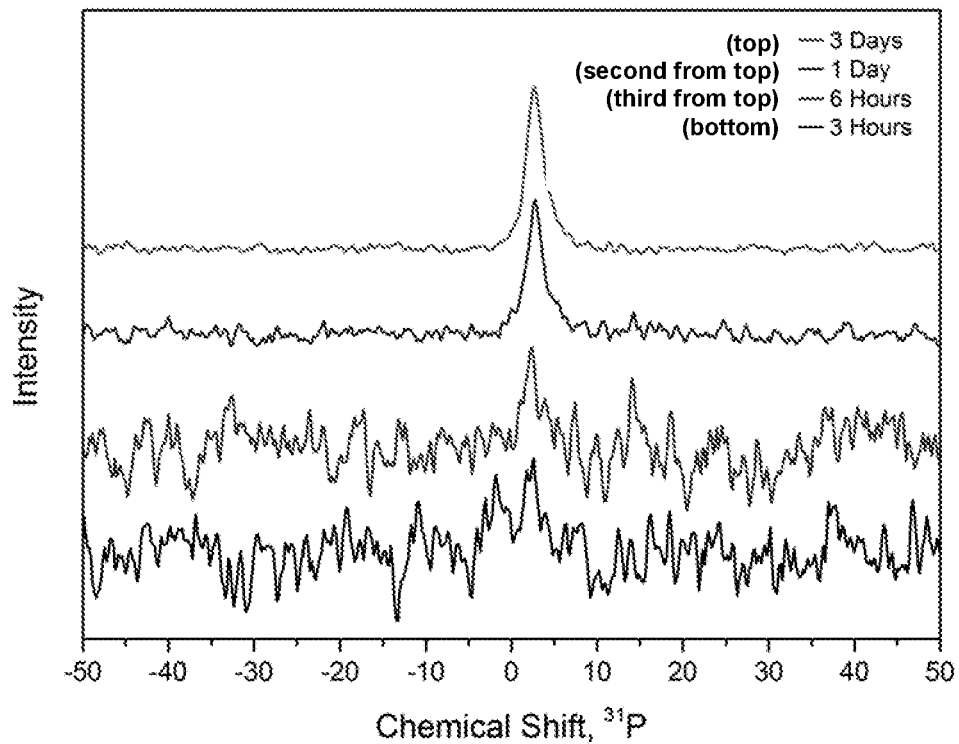
FIG. 8: Shows the $^{31}P$ NMR spectra of Sample 2 after 3 hours, 6 hours, 1 day, 3 days immersion in SBF solution.
Figure 9:
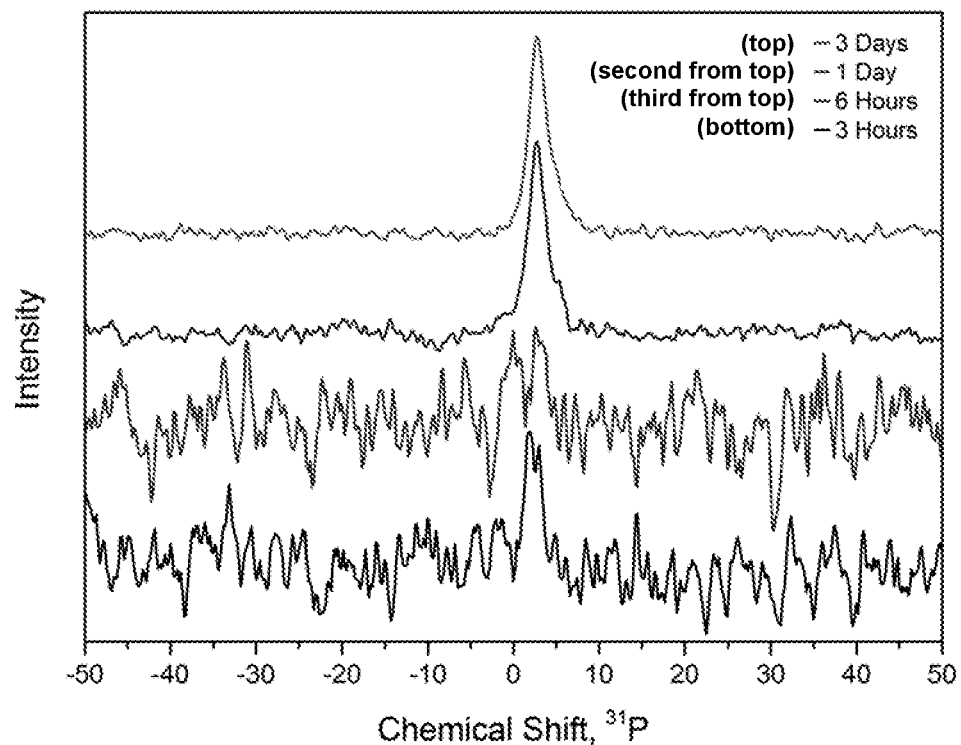
FIG. 9: Shows the $^{31}P$ NMR spectra of Sample 4 after 3 hours, 6 hours, 1 day, 3 days immersion in SBF solution.
Figure 10:
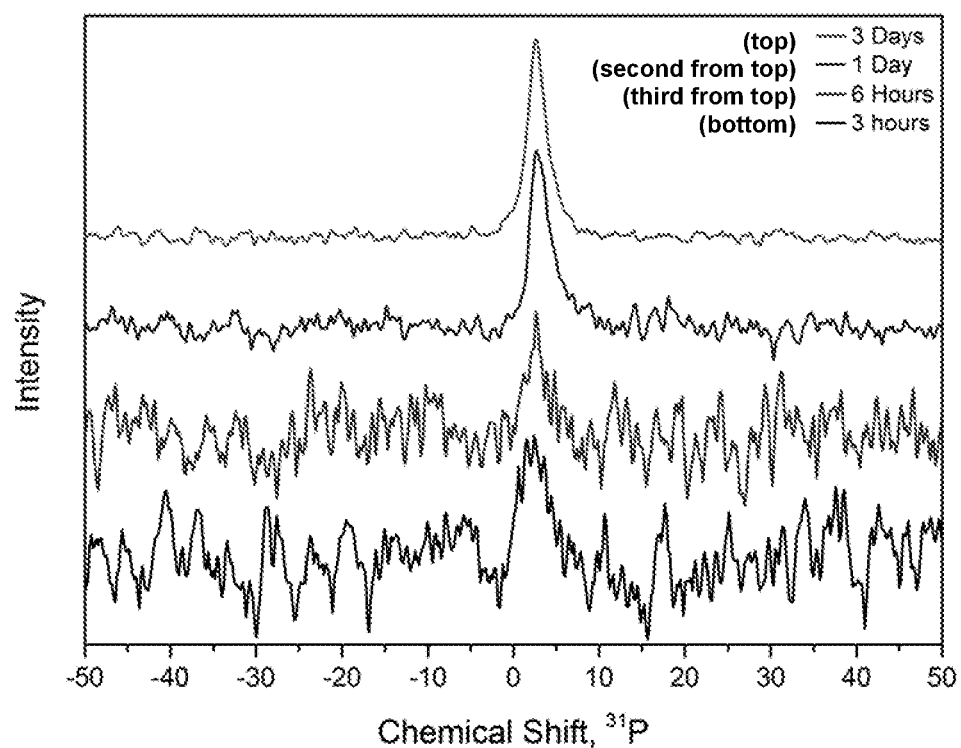
FIG. 10: Shows the $^{31}P$ NMR spectra of Sample 5 after 3 hours, 6 hours, 1 day, 3 days immersion in SBF solution.
Figure 11:
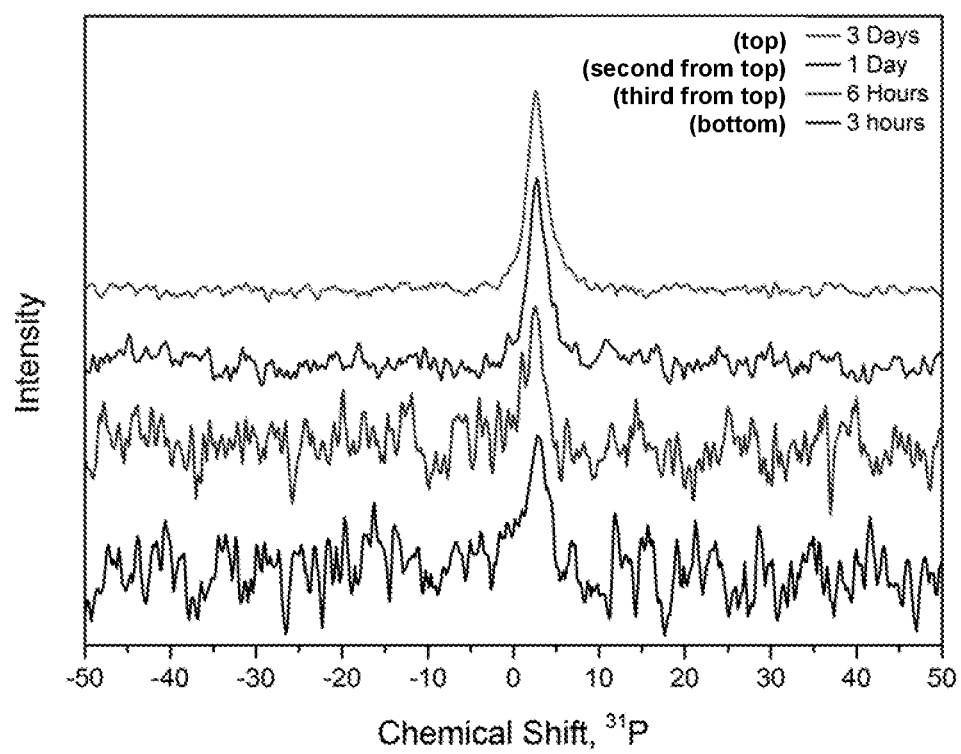
FIG. 11: Shows the $^{31}P$ NMR spectra of Sample 6 after 3 hours, 6 hours, 1 day, 3 days immersion in SBF solution.

FIGS. 3 and 4 show a scanning electron micrograph of sample 2 after calcination.

The structure of the unreacted sample 2 shows silica spheres forming a bioactive aerogel structure.

This data demonstrates that the bone graft substitutes of the present invention are bioactive and exhibit low densities and high surface areas, compared to typically used bones graft substitutes.

Example 5

$^{31}$P magic angle spinning nuclear magnetic resonance (MAS-NMR) was performed on a Bruker 600 MHz spectrometer at the 242.9 MHz resonance frequency. The powder samples were packed into a 4 mm rotor and spun at 12 kHz. The measurements were done using 60 s recycle delay and 85% $H_3PO_4$ was used to reference the chemical shift scale.

FIGS. 7-11 show the $^{31}$P NMR spectra of samples 1, 2, 4, 5 and 6 (from table 1) respectively. Measurements were taken after 3 hours, 6 hours, 1 day and 3 days immersion in SBF solution.

A typical $^{31}$P shift at 2.9 ppm is beginning to appear after 3 hours with all samples and is clearly visible after 6 hours. This demonstrates that the material has the ability to form hydroxyapatite (or similar) structures on its surface. This is a standard test used to demonstrate the bioactivity of a material.

Example 7

Example 7 provides a method which can be used for producing bone graft substitutes of the present invention.

Reagents 0.14M NaF solution

Absolute (100%) ethanol tetraethyl orthosilicate (TEOS, $(Si(OC_2H_5)_4)$)

Brushite ($CaHPO_4 \cdot 2H_2O$) Brushite is dissolved in 0.14 M solution of NaF, after which ethanol is added. This mixture is then stirred for 5 minutes.

Finally the TEOS is combined slowly with the solution and is allowed to stir for thirty seconds.

4 ml of the solution is cast into cylindrical moulds (Ø11 mm×50 mm height, via syringe). Each mould is then covered with film and placed into glass container.

Each sample is then gelled for 48 hours at 60° C.

Each sample is then placed into 60% ethanol. After 24 hours the solution is changed for 80% ethanol. After another 24 hours it is changed once again for 95% ethanol. Finally the solution is replaced with 100% ethanol.

Each sample is dried using the CPD method using a Tousimis® 931 critical point drier. Each sample is run through three stasis cycles of eight hours each.

After critical drying each sample is then calcined at 700° C. for three hours.

Example 8

The compositions outlined in table 3 may be produced by the method of example 6.

TABLE 3

Chemical compositions

| Composition | SiO$_2$ (mol %) | P$_2$O$_5$ (mol %) | CaO (mol %) |
| --- | --- | --- | --- |
| Sample 7 | 60.00 | 13.33 | 26.67 |
| Sample 8 | 65.00 | 11.66 | 23.34 |
| Sample 9 | 70.00 | 10.00 | 20.00 |

Example 9

Example 9 provides a method which can be used for producing bone graft substitutes of the present invention.

Reagents 0.14M NaF solution

Absolute (100%) ethanol tetraethyl orthosilicate (TEOS, $(Si(OC_2H_5)_4)$)

Brushite ($CaHPO_4 \cdot 2H_2O$)

Calcium nitrate tetrahydrate ($Ca(NO_3)_2 \cdot 4H_2O$)

Brushite is dissolved in 0.14 M solution of NaF, after which ethanol is added. The mixture is then stirred for 5 minutes, calcium nitrate tetrahydrate is then added to the mixture and left to dissolve for 5 minutes.

Finally the TEOS is combined slowly with the solution and allowed to stir for thirty seconds.

4 ml of the solution is cast into cylindrical moulds (Ø11 mm×50 mm height, via syringe). Each mould is then covered with film and placed into glass container.

Each sample is then gelled for 48 hours at 60° C.

Each sample is then placed into 60% ethanol. After 24 hours the solution is changed for 80% ethanol. After another 24 hours it is changed once again for 95% ethanol. Finally the solution is replaced with 100% ethanol.

Each sample is dried using the CPD method using a Tousimis® 931 critical point drier. Each sample is run through three stasis cycles of eight hours each.

After critical drying each sample is then calcined at 700° C. for three hours.

The invention claimed is:

1. A bioactive bone graft substitute comprising a silicate based material which is a silicate network having a porous structure wherein one or more metal cations are incorporated into the silicate network and wherein the density of the bone graft substitute is less than 0.7 g/cm$^3$ and the average pore diameter of the bone graft substitute is from about 1 to about 99 nm, wherein the metal cations are ionically bound to the silicate network, and wherein the metal cations comprise calcium.

2. The bone graft substitute of claim 1 wherein the silicate network comprises between 0.01 and 70 mol % of metal cation.

3. The bone graft substitute of claim 1, wherein a phosphate is also incorporated into the silicate network.

4. The bone graft substitute of claim 3 wherein the silicate network comprises between 1 and 20 mol % of phosphate.

5. The bone graft substitute of claim 1, wherein the metal cations are ionically bound to the silicate network via an oxygen anion.

6. The bones graft substitute of claim 3, wherein the phosphate is ionically bound to the silicate network via one or more of the metal cations.

7. The bone graft substitute of claim 3, wherein the phosphate is a $PO_4^{3-}$ anion.

8. The bone graft substitute of claim 3, wherein the phosphate is covalently bound to the silicate network via a Si—O—P covalent bond.

9. The bone graft substitute of claim 1, wherein the bone graft substitute is a porous solid gel, wherein the porous solid gel has a gas as the dispersed phase, an aerogel, or a cryogel.

10. The bone graft substitute of claim 1, wherein the metal cation is calcium and optionally one or more of strontium, sodium, zinc, magnesium, potassium, titanium, cobalt, aluminum, silver.

11. The bone graft substitute of claim 1, wherein the silicate to metal cation ratio is between 0.3 and 2.

12. The bone graft substitute of claim 1, wherein the bone graft substitute contains between 10 and 70 mol % of metal cation.

13. The bone graft substitute of claim 1, wherein the metal cation is derived in whole or in part from any one of hydroxyapatite $(Ca_{10})(PO_4)_6(OH)_2)$, hydroxycarbonatedapatite octacalcium phosphate $(Ca_8H_2(PO_4)_6 \cdot 5H_2)$, brushite $(CaHPO_4 \cdot 2H_2O)$, monetite $(CaHPO_4)$, fluorapatite $(Ca_{10})(PO_4)_6F_2)$, chlorapatite $(Ca_{10})(PO_4)_6Cl_2)$, fluorohydroxyapatite $(Ca_{10}(PO_4)_6(OH)_{2-x}F_x)$, tetracalcium phosphate $(Ca_4(PO_4)_2O)$, tricalcium phosphate $(Ca_3(PO_4)_2)$ or any combination thereof.

14. The bone graft substitute of claim 3, wherein the phosphate is $P_2O_5$.

15. The bone graft substitute of claim 3, wherein the metal cation to phosphate ratio is between 0.2 and 20.

16. The bone graft substitute of claim 3 wherein the bone graft substitute contains between 1 and 20 mol % of phosphate.

17. The bones graft substitute of claim 3, wherein the phosphate is derived in whole or in part from any one of hydroxyapatite $(Ca_{10})(PO_4)_6(OH)_2)$, hydroxycarbonatedapatite octacalcium phosphate $(Ca_8H_2(PO_4)_6 \cdot 5H_2O)$, brushite $(CaHPO_4 \cdot 2H_2O)$, monetite $(CaHPO_4)$, fluorapatite $(Ca_{10})(PO_4)_6F_2)$, chlorapatite $(Ca_{10})(PO_4)_6Cl_2)$, fluorohydroxyapatite $(Ca_{10}(PO_4)_6(OH)_{2-x}F_x)$, tetracalcium phosphate $(Ca_4(PO_4)_2O)$, tricalcium phosphate $(Ca_3(PO_4)_2)$ or any combination thereof.

18. The bone graft substitute of claim 1, wherein the silicate is a silicon oxide or a silicon fluoride.

19. The bone graft substitute of claim 18 wherein the silicate is a silicon oxide.

20. The bone graft substitute of claim 19 wherein the silicon oxide is $SiO_2$.

21. The bone graft substitute of claim 1, wherein the bone graft substitute contains between 20 and 80 mol % of silicate.

22. The bone graft substitute of claim 1, wherein the bone graft substitute further comprises hydroxyapatite $(Ca_{10})(PO_4)_6(OH)_2)$, hydroxycarbonatedapatite octacalcium phosphate $(Ca_8H_2(PO_4)_6 \cdot 5H_2O)$, brushite $(CaHPO_4 \cdot 2H_2O)$, monetite $(CaHPO_4)$, fluorapatite $(Ca_{10})(PO_4)_6F_2)$, chlorapatite $(Ca_{10})(PO_4)_6Cl_2)$, fluorohydroxyapatite $(Ca_{10}(PO_4)_6(OH)_{2-x}F_x)$, tetracalcium phosphate $(Ca_4(PO_4)_2O)$, tricalcium phosphate $(Ca_3(PO_4)_2)$ or any combination thereof.

23. The bone graft substitute of claim 1, having a density of less than 0.3 g/cm$^3$.

24. The bone graft substitute of claim 1, having a density of greater than 0.001 g/cm$^3$.

25. The bone graft substitute of claim 24 having an average pore diameter from about 10 to about 25 nm.

26. The bone graft substitute of claim 1, having a pore volume from about 1 to about 20 cm$^3$/g.

27. The bone graft substitute of claim 26 having a pore volume from about 4 to about 8 cm$^3$/g.

28. The bone graft substitute of claim 1, having a surface area greater than 400 m$^2$/g.

29. The bone graft substitute of claim 28 having a surface area greater than 850 m$^2$/g.

30. A process of making the bioactive bone graft substitute of claim 1 comprising:
    (i) a gel formation stage;
    (ii) a liquid phase replacement stage;
    (iii) a gel drying stage; and
    (iv) a calcination stage;
    wherein the gel formation stage comprises the steps of dissolving a metal cation in a first solvent, adding a silicate to the solvent and gelling of the resultant mixture; and
    wherein the liquid phase replacement stage comprises the step of soaking the gel in a second solvent; and
    wherein the gel drying stage is carried out by freeze-drying or supercritical drying; and
    wherein the calcination stage comprises the step of heating the dried gel.

31. The process of claim 30 wherein the gel formation step further comprises the step of dissolving a phosphate in the first solvent before adding the silicate.

32. The process of claim 30, wherein the gel formation step further comprises the step of adding any one of hydroxyapatite $(Ca_{10})(PO_4)_6(OH)_2)$, hydroxycarbonatedapatite octacalcium phosphate $(Ca_8H_2(PO_4)_6 \cdot 5H_2O)$, brushite $(CaHPO_4 \cdot 2H_2O)$, monetite $(CaHPO_4)$, fluorapatite $(Ca_{10})(PO_4)_6F_2)$, chlorapatite $(Ca_{10})(PO_4)_6Cl_2)$, fluorohydroxyapatite $(Ca_{10}(PO_4)_6(OH)_{2-x}F_x)$, tetracalcium phosphate $(Ca_4(PO_4)_2O)$, tricalcium phosphate $(Ca_3(PO_4)_2)$ or any combination thereof to the first solvent.

33. The process of claim 30 wherein the second solvent is an organic solvent.

34. The process of claim 33 wherein the second solvent is ethanol.

35. The process of claim 30, wherein the calcination stage is carried out at a temperature of at least 400 K.

36. The process of claim 30, wherein the calcination stage may be carried out for at least 1 hour.

37. The process of claim 30, wherein the metal cation is provided by a metal salt.

38. The process of claim 37 wherein the metal cation is provided by a calcium salt.

39. The process of claim 38 wherein the calcium salt is selected from calcium nitrate tetrahydrate, calcium acetate and calcium nitrate.

40. The process of claim 30, wherein the metal cation is provided in whole or in part by any one of hydroxyapatite $(Ca_{10})(PO_4)_6(OH)_2)$, hydroxycarbonatedapatite octacalcium phosphate $(Ca_8H_2(PO_4)_6 \cdot 5H_2O)$, brushite $(CaHPO_4 \cdot 2H_2O)$, monetite $(CaHPO_4)$, fluorapatite $(Ca_{10})(PO_4)_6F_2)$, chlorapatite $(Ca_{10})(PO_4)_6Cl_2)$, fluorohydroxyapatite $(Ca_{10}(PO_4)_6(OH)_{2-x}F_x)$, tetracalcium phosphate $(Ca_4(PO_4)_2O)$, tricalcium phosphate $(Ca_3(PO_4)_2)$ or any combination thereof.

41. The process of 36, wherein the phosphate is provided by triethylphosphate.

42. The process of claim 31, wherein the phosphate is provided in whole or in part by any one of hydroxyapatite $(Ca_{10})(PO_4)_6(OH)_2)$, hydroxycarbonatedapatite octacalcium phosphate $(Ca_8H_2(PO_4)_6 \cdot 5H_2O)$, brushite $(CaHPO_4 \cdot 2H_2O)$, monetite $(CaHPO_4)$, fluorapatite $(Ca_{10})(PO_4)_6F_2)$, chlorapatite $(Ca_{10})(PO_4)_6Cl_2)$, fluorohydroxyapatite $(Ca_{10}(PO_4)_6(OH)_{2-x}F_x)$, tetracalcium phosphate $(Ca_4(PO_4)_2O)$, tricalcium phosphate $(Ca_3(PO_4)_2)$ or any combination thereof.

43. A composition comprising the bone graft substitute of claim 1 and at least one other biomaterial.

44. The composition of claim 43 wherein the at least one biomaterial comprises hydroxyapatite $(Ca_{10})(PO_4)_6(OH)_2)$, hydroxycarbonatedapatite octacalcium phosphate $(Ca_8H_2(PO_4)_6 \cdot 5H_2O)$, brushite $(CaHPO_4 \cdot 2H_2O)$, monetite $(CaHPO_4)$, fluorapatite $(Ca_{10})(PO_4)_6F_2)$, chlorapatite $(Ca_{10})(PO_4)_6Cl_2)$, fluorohydroxyapatite $(Ca_{10}(PO_4)_6(OH)_{2-x}F_x)$, tetracalcium phosphate $(Ca_4(PO_4)_2O)$, tricalcium phosphate $(Ca_3(PO_4)_2)$ or any combination thereof.

45. A method of promoting bone growth in a void, cavity, or fracture site in a subject, comprising:
introducing a bone graft substitute of claim 1 into said void, cavity, or fracture site.

46. The bone graft substitute of claim 1, further comprising fluoride.

47. A toothpaste comprising the bone graft substitute of claim 1.

* * * * *